US010806429B2

(12) United States Patent
Takano

(10) Patent No.: US 10,806,429 B2
(45) Date of Patent: Oct. 20, 2020

(54) ULTRASONIC IMAGING DEVICE AND ULTRASONIC PROBE

(71) Applicant: Hitachi, Ltd., Chiyoda-ku, Tokyo (JP)

(72) Inventor: Shinta Takano, Tokyo (JP)

(73) Assignee: Hitachi, Ltd., Tokyo (JP)

( * ) Notice: Subject to any disclaimer, the term of this patent is extended or adjusted under 35 U.S.C. 154(b) by 473 days.

(21) Appl. No.: 15/750,011

(22) PCT Filed: Jul. 26, 2016

(86) PCT No.: PCT/JP2016/071912
§ 371 (c)(1),
(2) Date: Feb. 7, 2018

(87) PCT Pub. No.: WO2017/026278
PCT Pub. Date: Feb. 16, 2017

(65) Prior Publication Data
US 2018/0214123 A1    Aug. 2, 2018

(30) Foreign Application Priority Data

Aug. 7, 2015   (JP) .................................. 2015-157648

(51) Int. Cl.
*A61B 8/14*     (2006.01)
*G01S 7/52*     (2006.01)
(Continued)

(52) U.S. Cl.
CPC .............. *A61B 8/14* (2013.01); *A61B 8/0883* (2013.01); *A61B 8/4405* (2013.01);
(Continued)

(58) Field of Classification Search
CPC ....... G10K 11/346; A61B 8/14; A61B 8/0883; A61B 8/4405; G01S 15/8925;
(Continued)

(56) References Cited

U.S. PATENT DOCUMENTS 4,218,768 A  *  8/1980  Hassler ................ G01N 29/262
                                                    367/105
5,784,336 A  *  7/1998  Gopinathan .............. G01S 3/82
                                                    367/103
(Continued)

FOREIGN PATENT DOCUMENTS

JP       62-123819 A      6/1987
JP       2005-270423 A    10/2005
(Continued)

OTHER PUBLICATIONS

International Preliminary Report on Patentability (PCT/IB/373) issued in PCT Application No. PCT/JP2016/071912 dated Feb. 22, 2018, including English translation of Document C2 (Japanese-language Written Opinion (PCT/ISA/237)) filed on Feb. 2, 2018 (Six (6) pages).

(Continued)

*Primary Examiner* — Katherine L Fernandez
*Assistant Examiner* — Yi-Shan Yang
(74) *Attorney, Agent, or Firm* — Crowell & Moring LLP

(57) ABSTRACT

An ultrasonic imaging apparatus includes an ultrasonic probe and a delay amount calculation unit. Each of the delay circuits is configured to allow a first delay amount and a second delay amount to be set for each of the delay circuits, and delays a signal by a delay amount obtained by adding the first delay amount and the second delay amount together. The delay amount calculation unit calculates the first delay amount and the second delay amount such that a sum of the first delay amount and the second delay amount set for each of the delay circuits is equal to or less than a predefined maximum delay amount.

13 Claims, 28 Drawing Sheets

(51) Int. Cl.
*G01S 15/89* (2006.01)
*G10K 11/34* (2006.01)
*A61B 8/00* (2006.01)
*A61B 8/08* (2006.01)

(52) U.S. Cl.
CPC .......... *G01S 7/5202* (2013.01); *G01S 7/5208* (2013.01); *G01S 7/52025* (2013.01); *G01S 15/8925* (2013.01); *G01S 15/8927* (2013.01); *G10K 11/346* (2013.01)

(58) Field of Classification Search
CPC .............. G01S 15/8927; G01S 7/5202; G01S 7/52025; G01S 7/5208
See application file for complete search history.

(56) References Cited

U.S. PATENT DOCUMENTS

| | | | |
|---|---|---|---|
| 6,013,032 A | 1/2000 | Savord | |
| 2008/0294050 A1 | 11/2008 | Shinomura et al. | |
| 2011/0224549 A1* | 9/2011 | Tsujita | ................ G01S 15/8977 600/443 |
| 2012/0099757 A1* | 4/2012 | Park | ...................... G06T 7/0016 382/100 |
| 2012/0277590 A1* | 11/2012 | Song | ................... G01S 7/52019 600/443 |
| 2013/0310695 A1 | 11/2013 | Hongou et al. | |
| 2015/0374335 A1* | 12/2015 | Brown | ................ G01S 15/8993 600/447 |
| 2016/0367223 A1* | 12/2016 | Honjo | ................ G01S 7/52088 |

FOREIGN PATENT DOCUMENTS

| | | |
|---|---|---|
| JP | 2011-24927 A | 2/2011 |
| JP | 2013-39277 A | 2/2013 |
| JP | 2015-116256 A | 6/2015 |
| WO | WO 2006/006460 A1 | 1/2006 |

OTHER PUBLICATIONS

International Search Report (PCT/ISA/210) issued in PCT Application No. PCT/JP2016/071917 dated Sep. 27, 2016 with English translation (4 pages).

Japanese-language Written Opinion (PCT/ISA/237) issued in PCT Application No. PCT/JP2016/071917 dated Sep. 27, 2016 (3 pages).

* cited by examiner

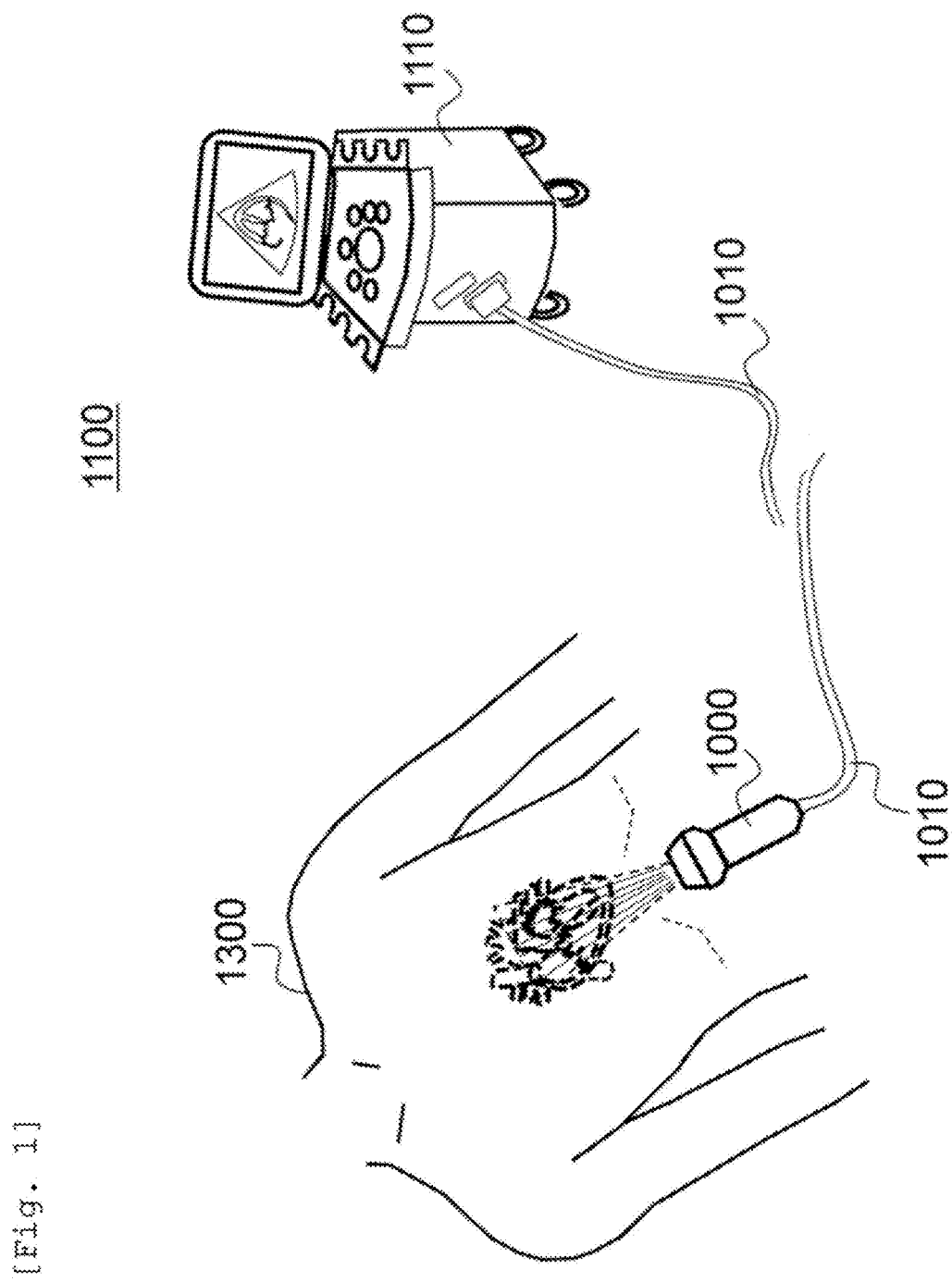
[Fig. 1]

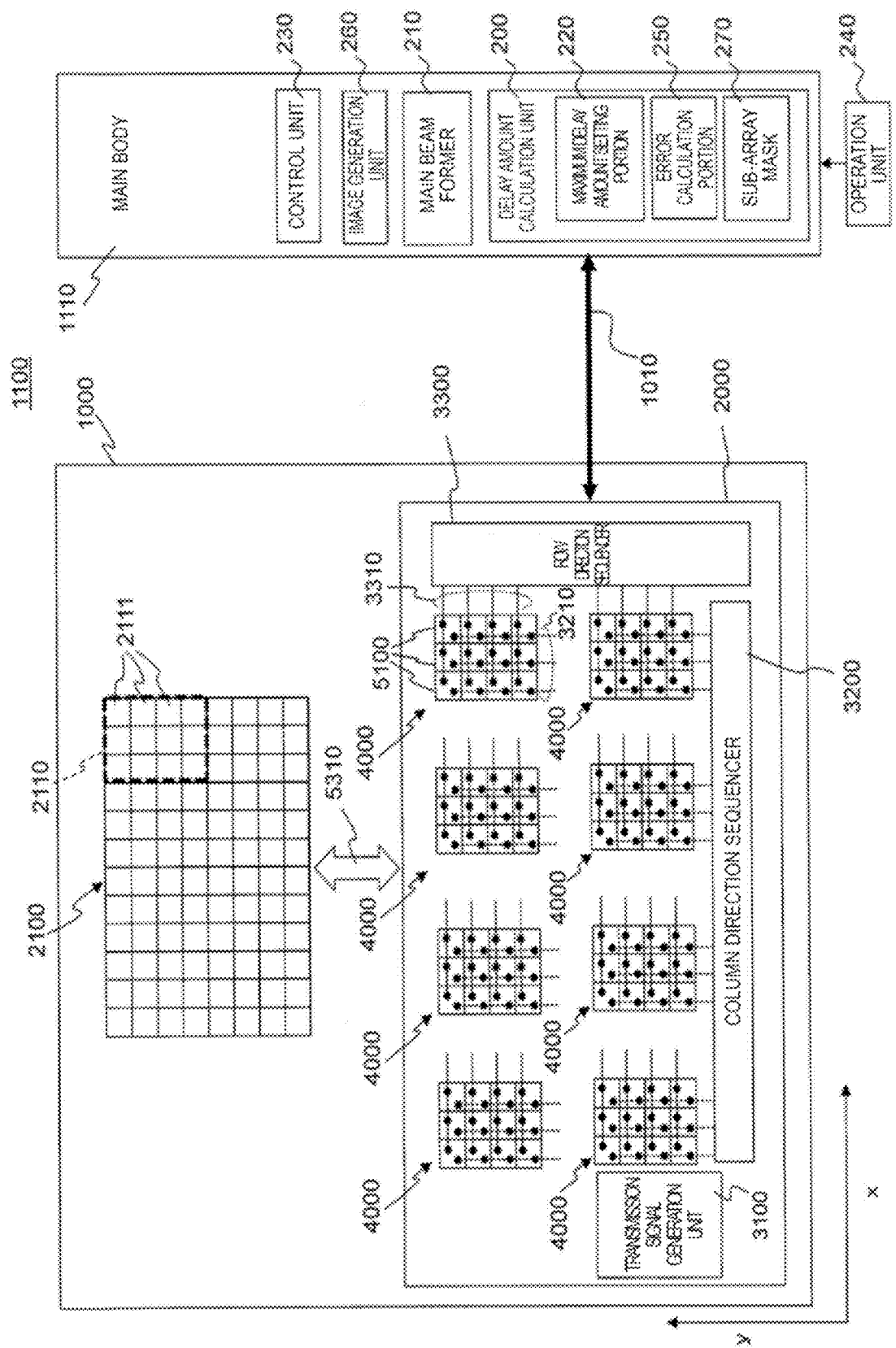
[Fig. 2]

[Fig. 3]
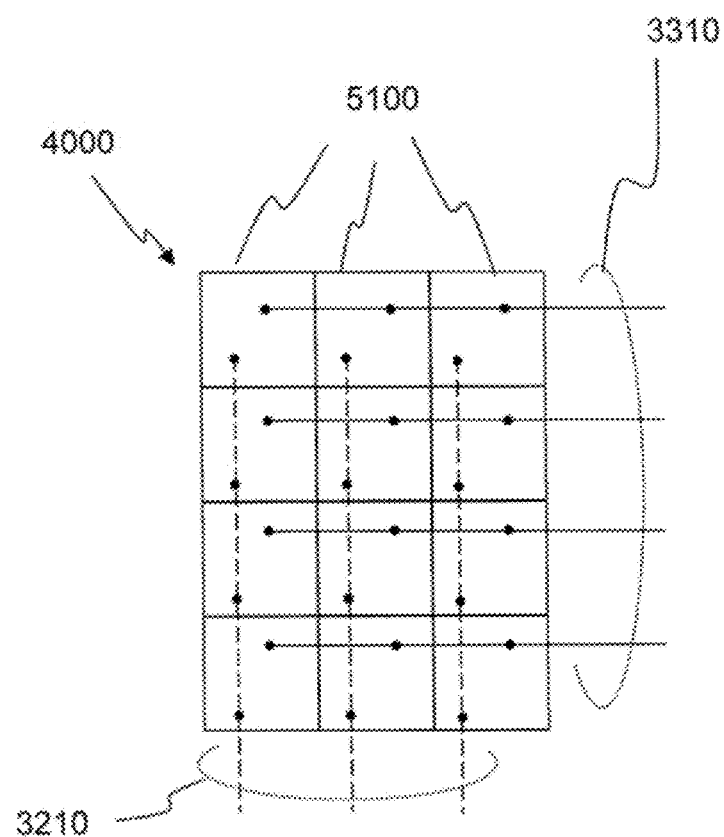

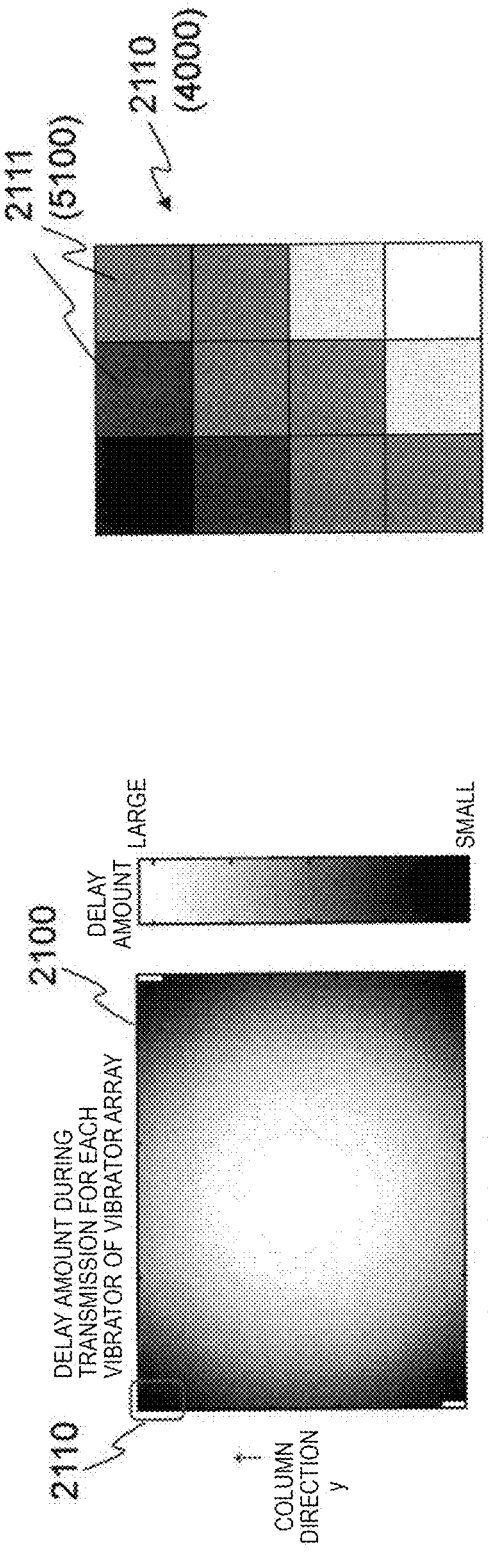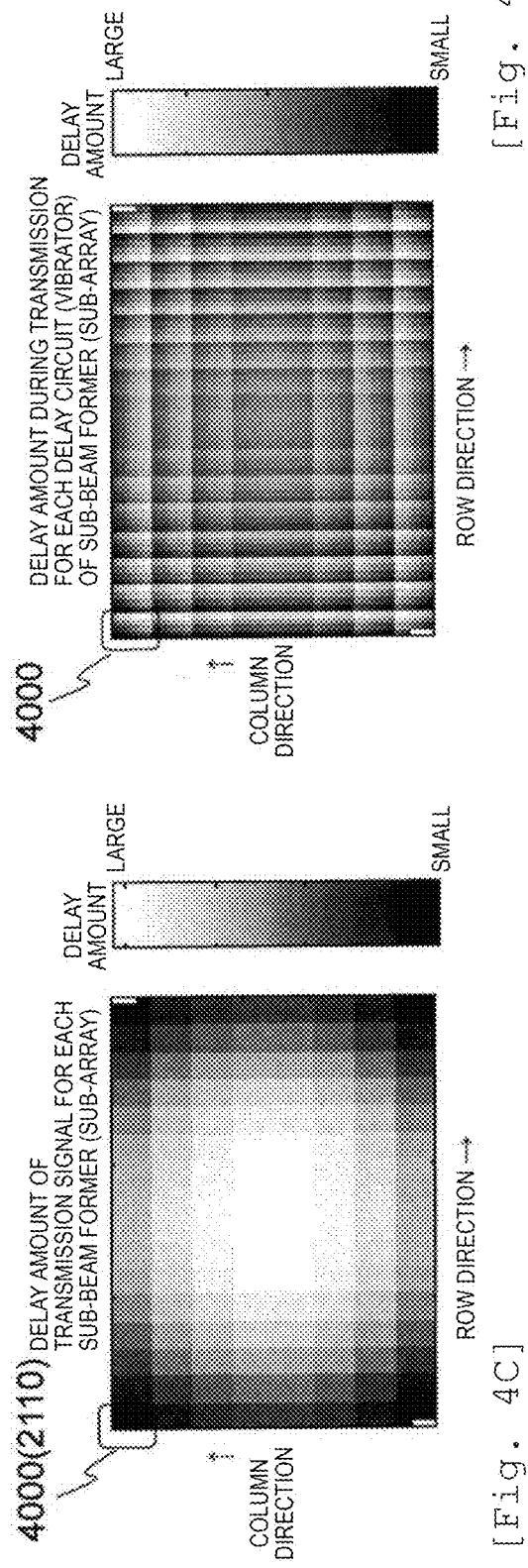

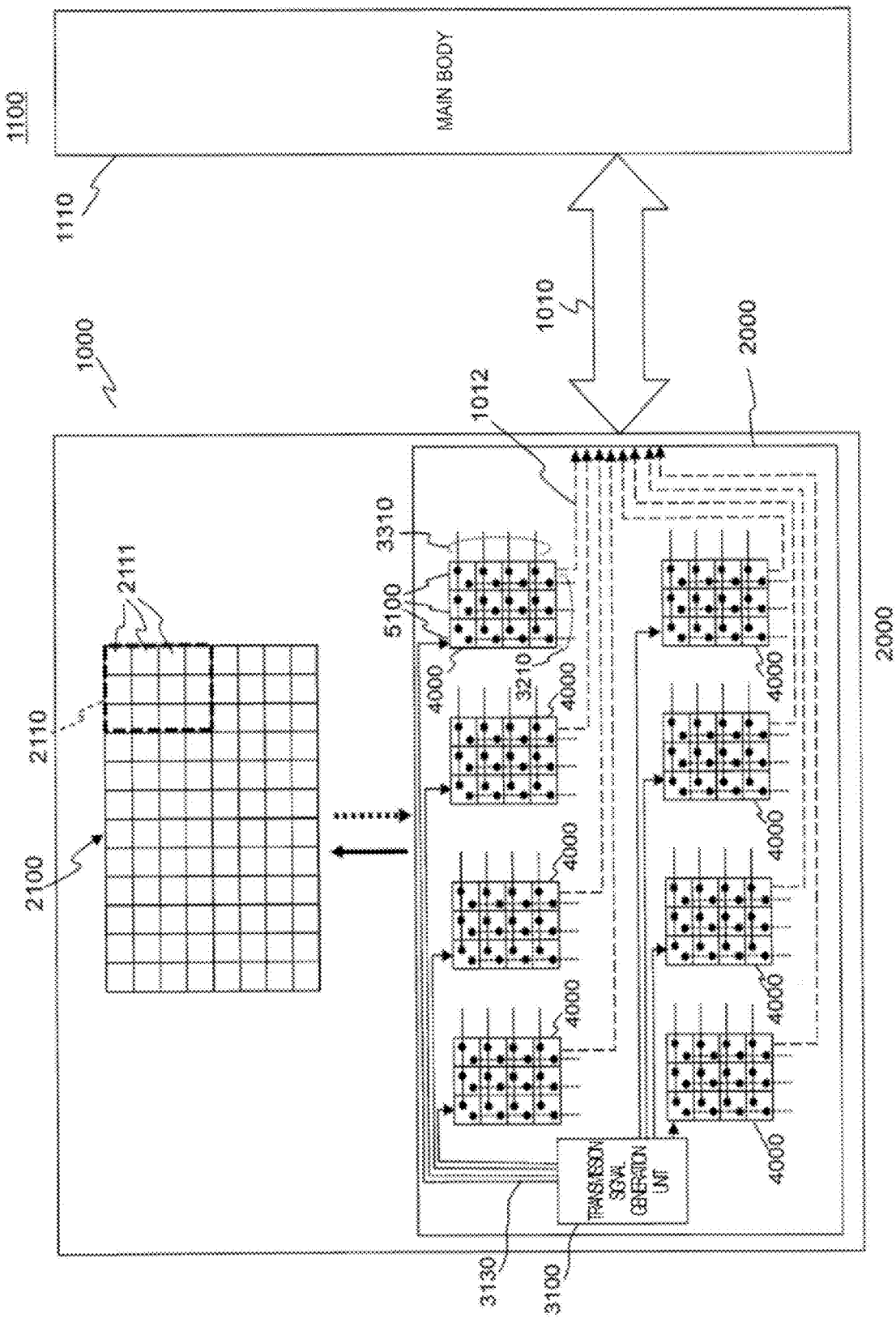
[Fig. 5]

[Fig. 6A] Delay amount during reception for each delay circuit (vibrator) of group (sub-array) 4000(2110) 2100

[Fig. 6B] 2111(5100) 2110(4000)

[Fig. 6C] Delay amount during reception in main beam former of main body 4000(2110)

[Fig. 6D] Delay amount of reception signal each vibrator of vibrator array 2100 2110

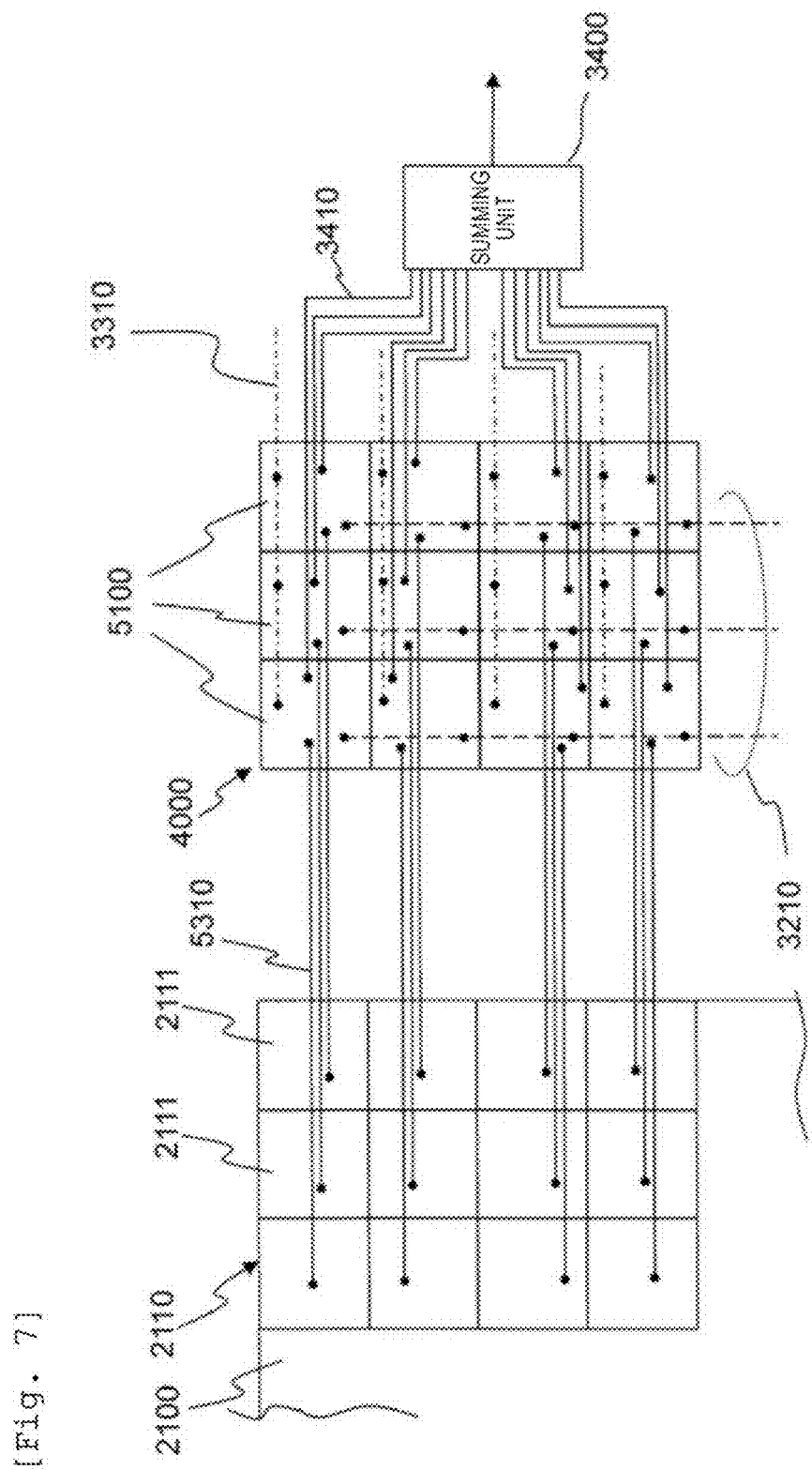

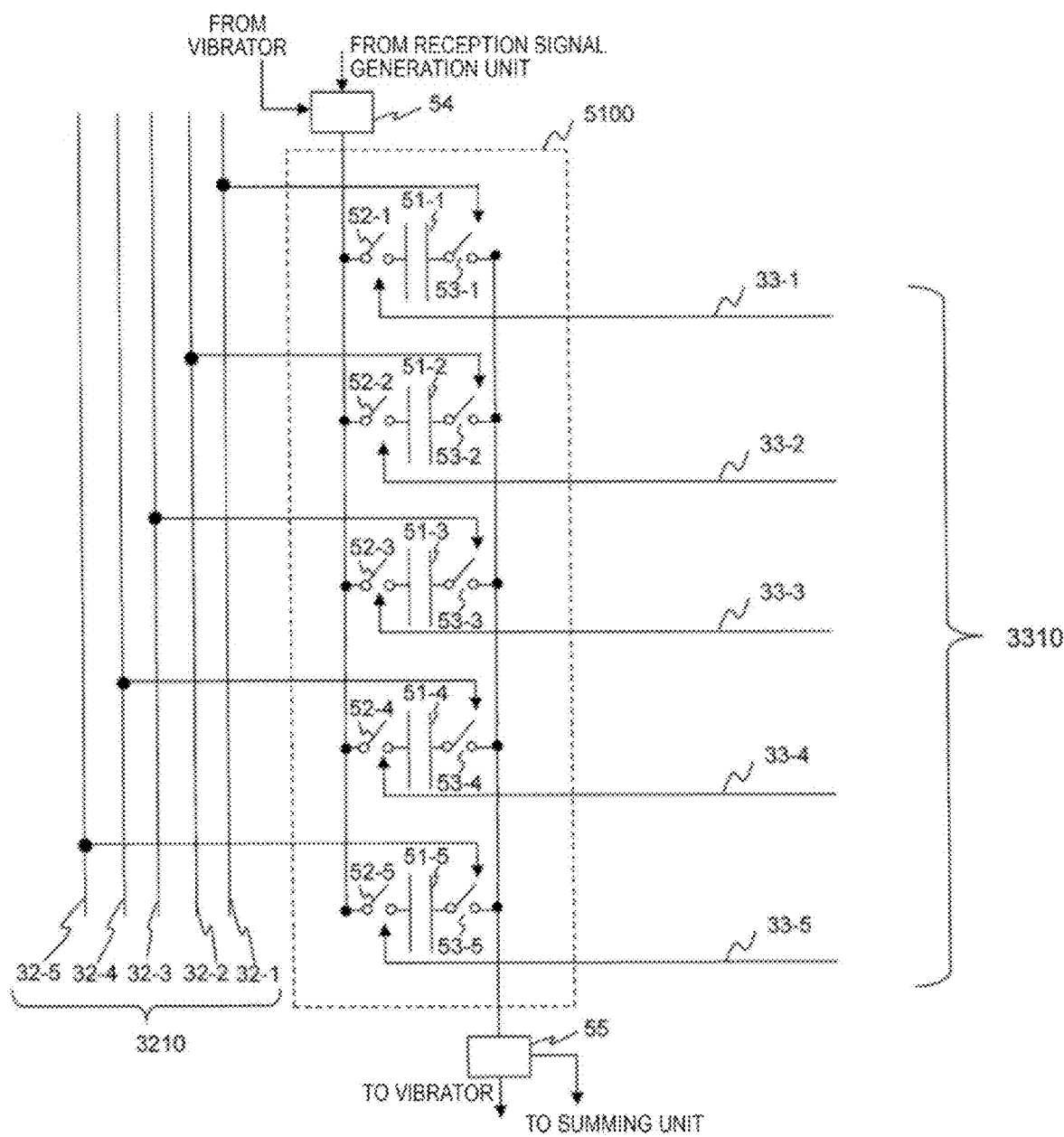
[Fig. 8]

[Fig. 9]
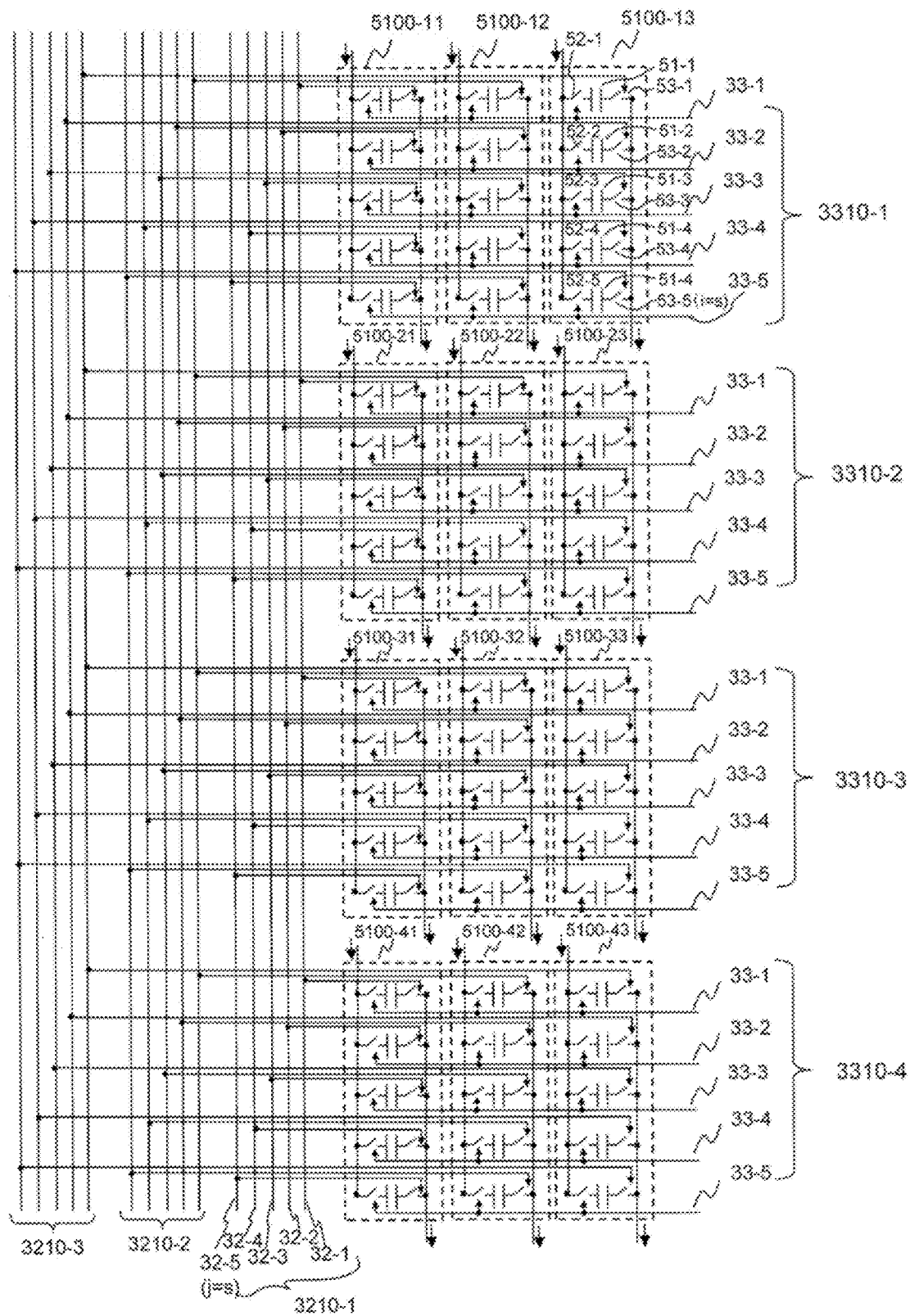

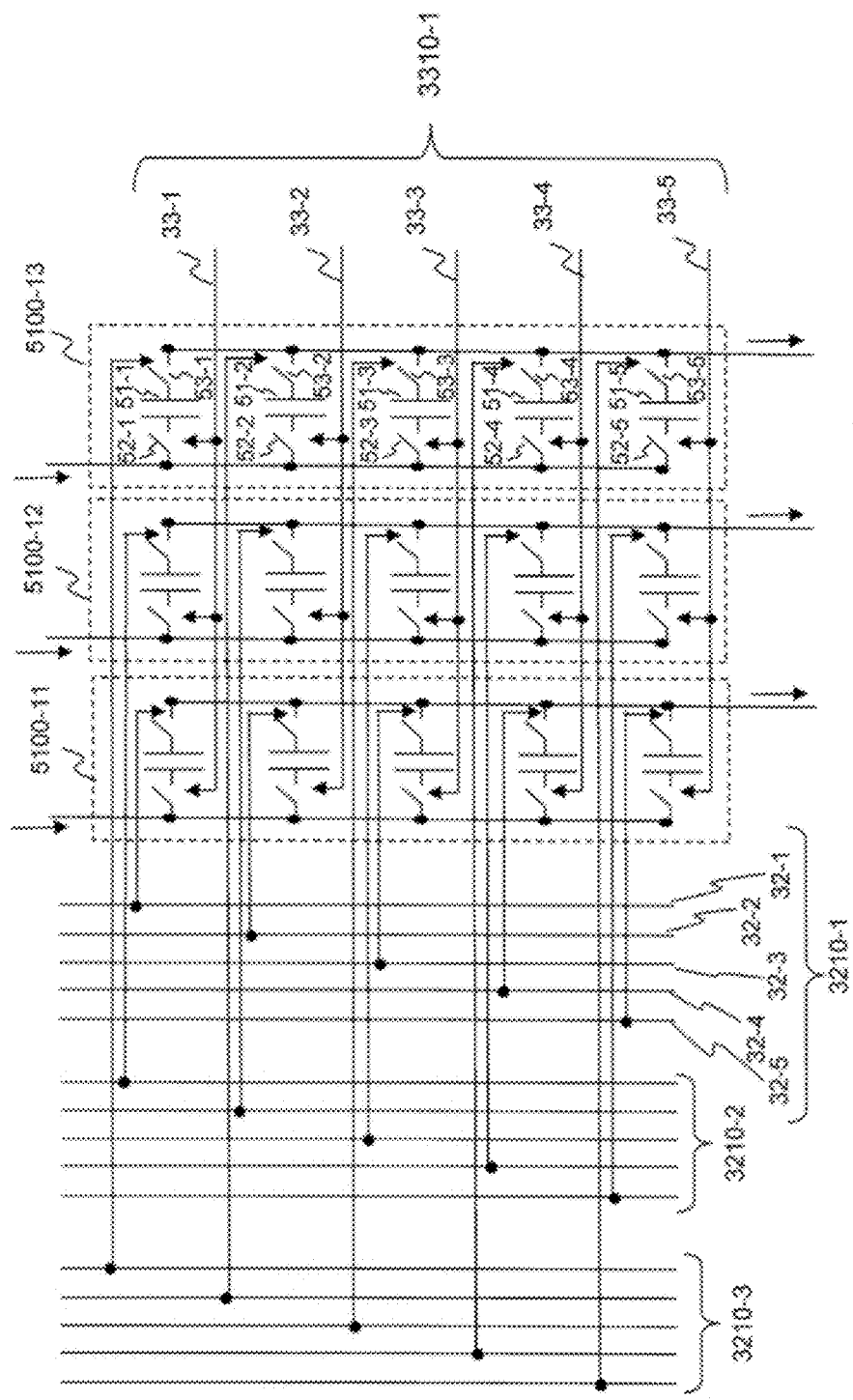
[Fig. 10]

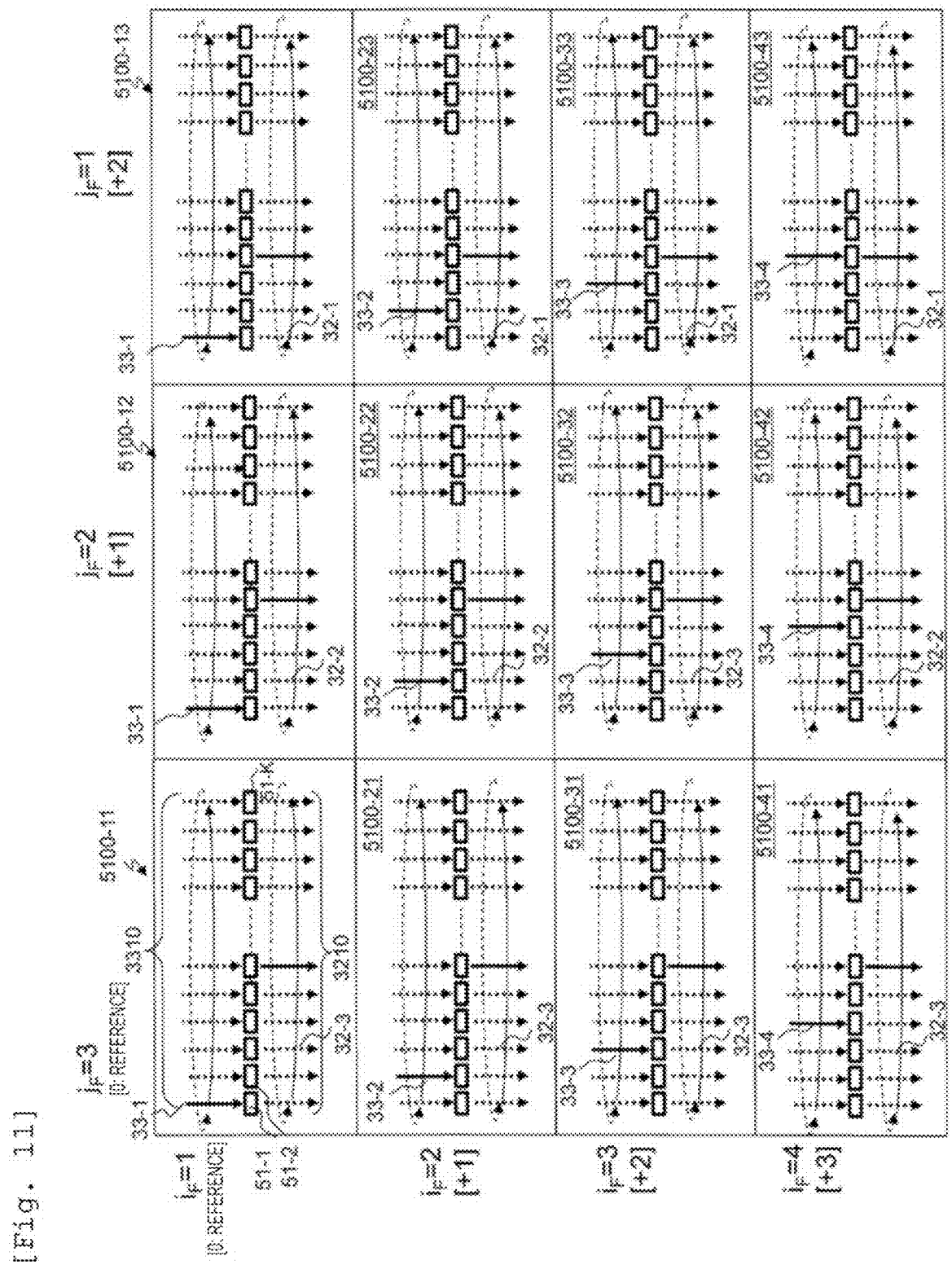

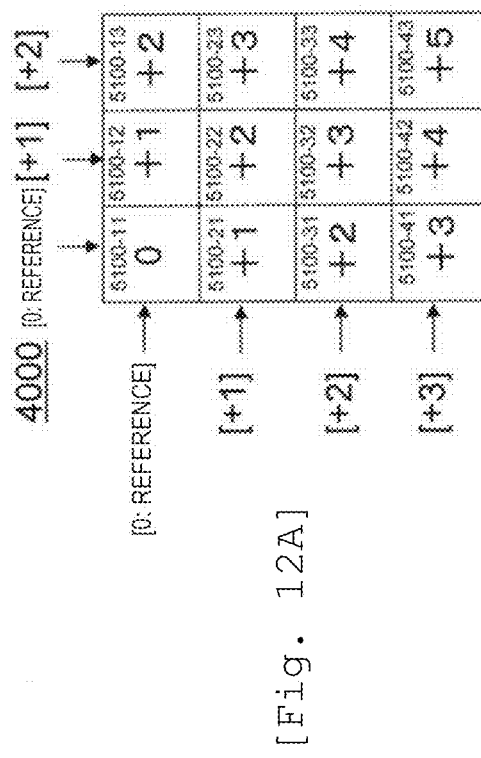
[Fig. 12A]
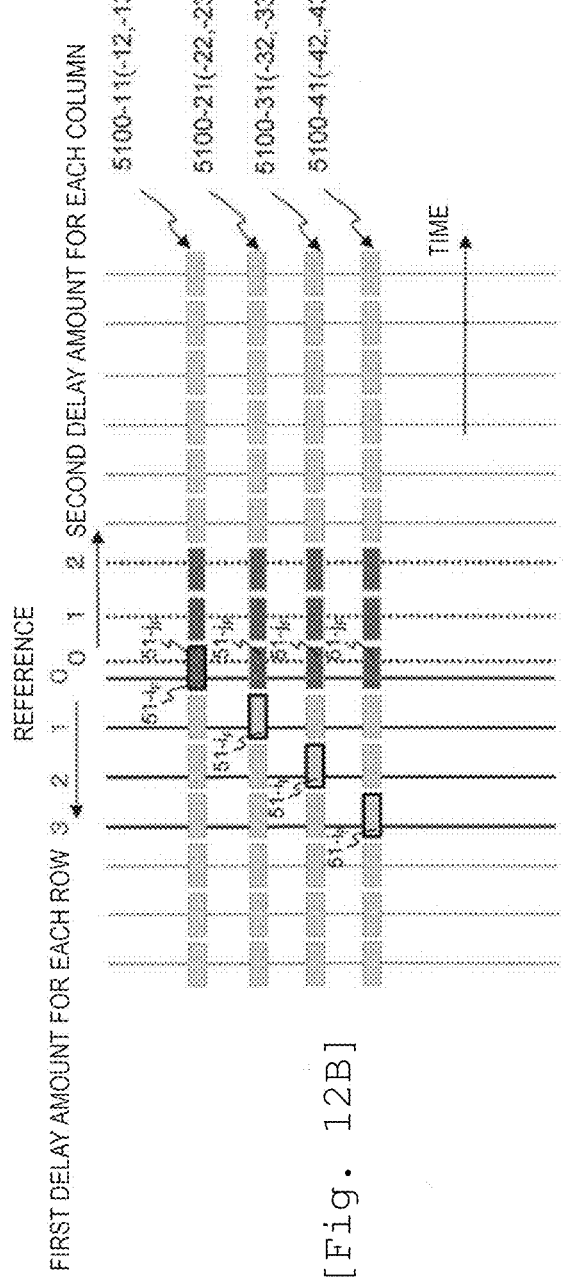
[Fig. 12B]

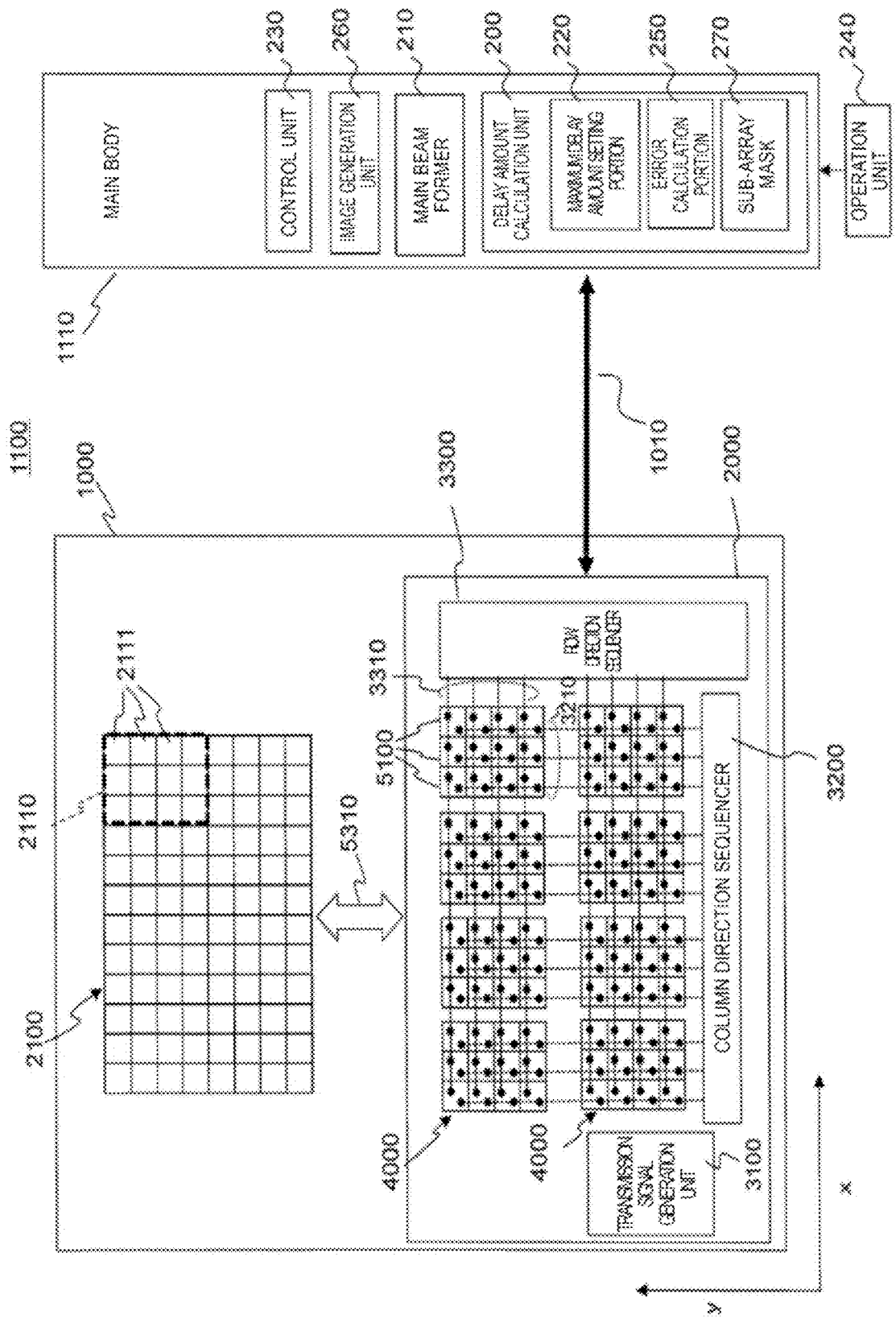
[Fig. 13]

[Fig. 14A]
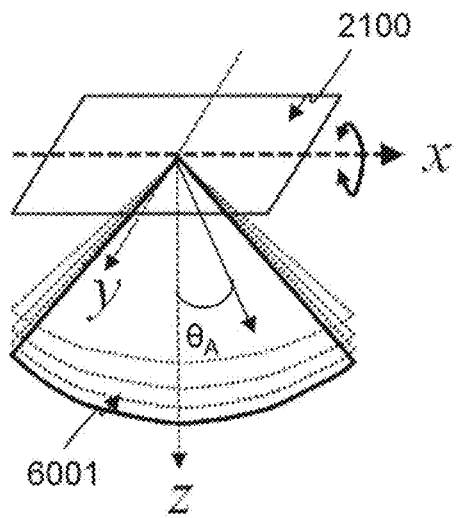
[Fig. 14B]
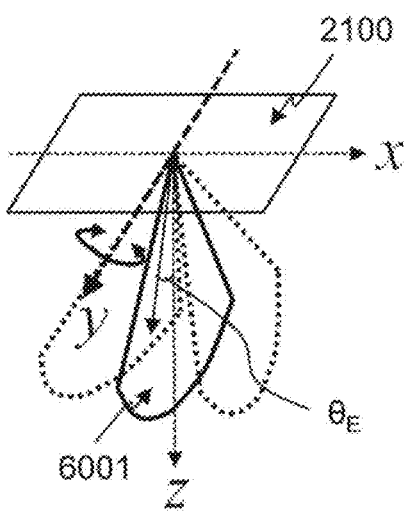
[Fig. 14C]
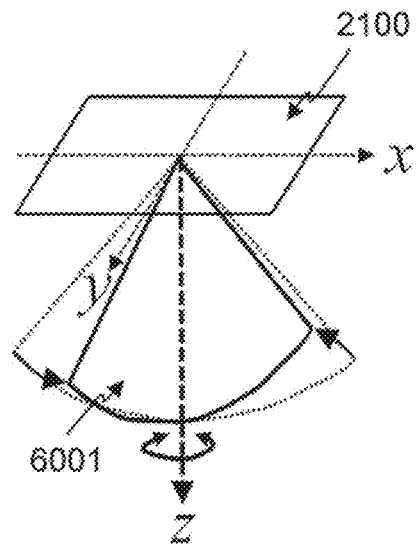
[Fig. 14D]
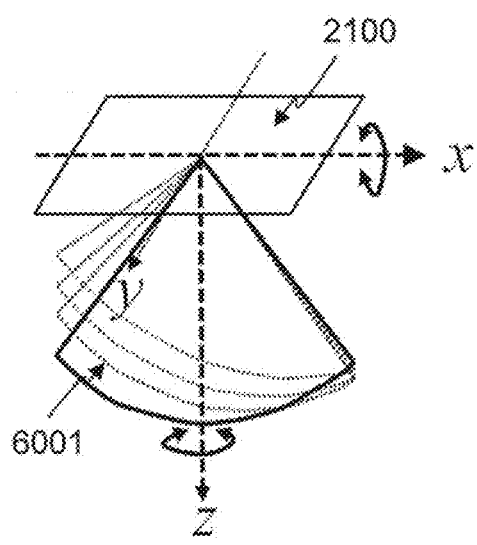

[Fig. 15A] TIME POINT 0

| 51-1 | 2 | 3 | 4 | 5 | |
|---|---|---|---|---|---|
| i | Null | Null | Null | Null | Null | ← 5100-11 |
| j | Null | Null | Null | Null | Null | ← 5100-21 |
| k | Null | Null | Null | Null | Null | ← 5100-31 |

[Fig. 15B] AFTER THREE CLOCKS

| | 1 | 2 | 3 | 4 | 5 |
|---|---|---|---|---|---|
| i | 0 | 1 | 2 | Null | Null |
| j | 1 | 2 | Null | Null | Null |
| k | 2 | Null | Null | Null | Null |

[Fig. 15C] AFTER FIVE CLOCKS

| | 1 | 2 | 3 | 4 | 5 |
|---|---|---|---|---|---|
| i | 0 | 1 | 2 | 3 | 4 |
| j | 1 | 2 | 3 | 4 | Null |
| k | 2 | 3 | 4 | Null | Null |

[Fig. 15D] AFTER SEVEN CLOCKS

| | 1 | 2 | 3 | 4 | 5 |
|---|---|---|---|---|---|
| i | 5 | 6 | 2 | 3 | 4 |
| j | 6 | 2 | 3 | 4 | 5 |
| k | 2 | 3 | 4 | 5 | 6 |

[Fig. 15E] AFTER TEN CLOCKS

| | 1 | 2 | 3 | 4 | 5 |
|---|---|---|---|---|---|
| i | 5 | 6 | 7 | 8 | 9 |
| j | 6 | 7 | 8 | 9 | 5 |
| k | 7 | 8 | 9 | 5 | 6 |

[Fig. 15F] AFTER FIFTEEN CLOCKS

| | 1 | 2 | 3 | 4 | 5 |
|---|---|---|---|---|---|
| i | 10 | 11 | 12 | 13 | 14 |
| j | 11 | 12 | 13 | 14 | 10 |
| k | 12 | 13 | 14 | 10 | 11 |

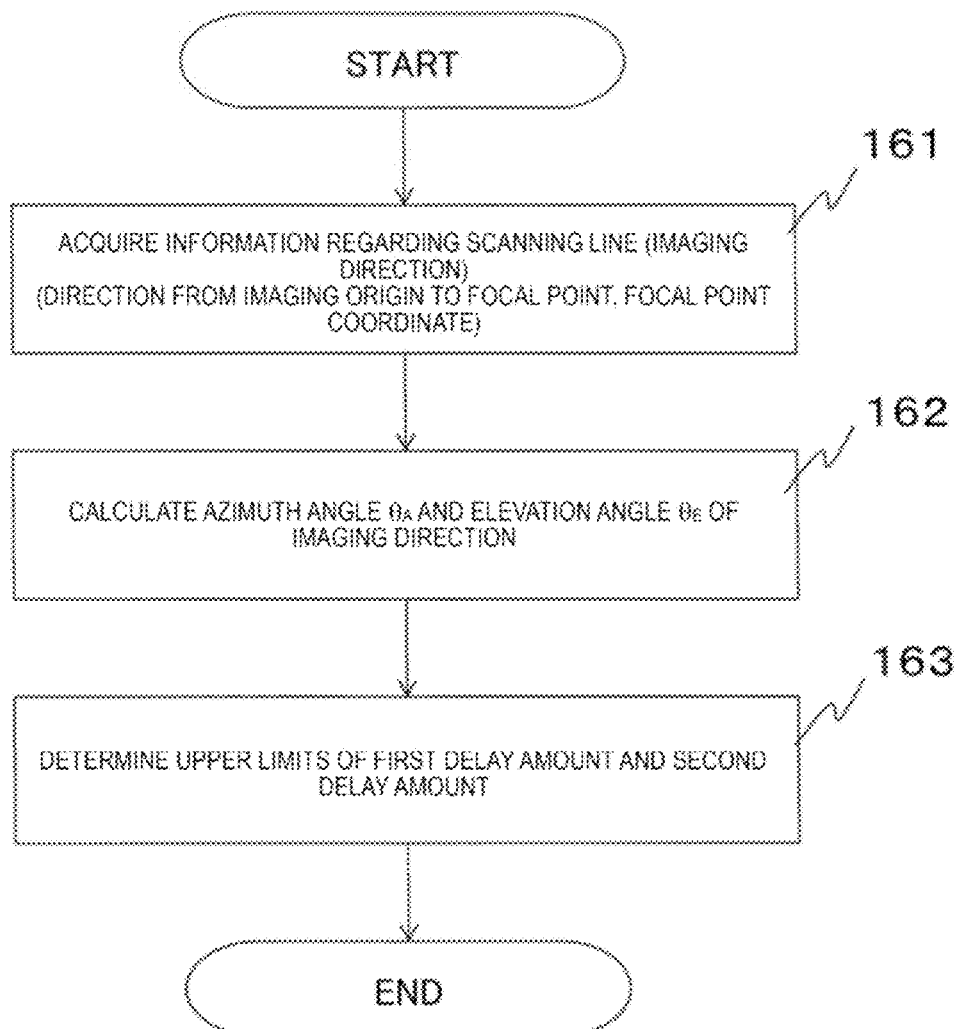
[Fig. 16]

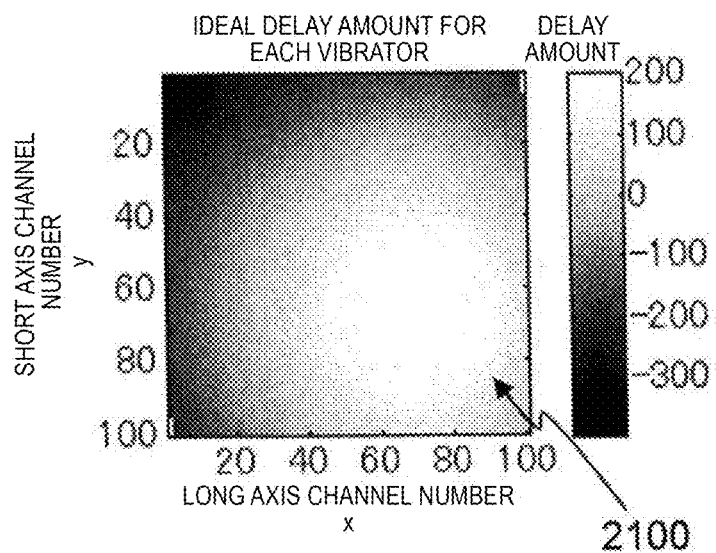
[Fig. 17A]
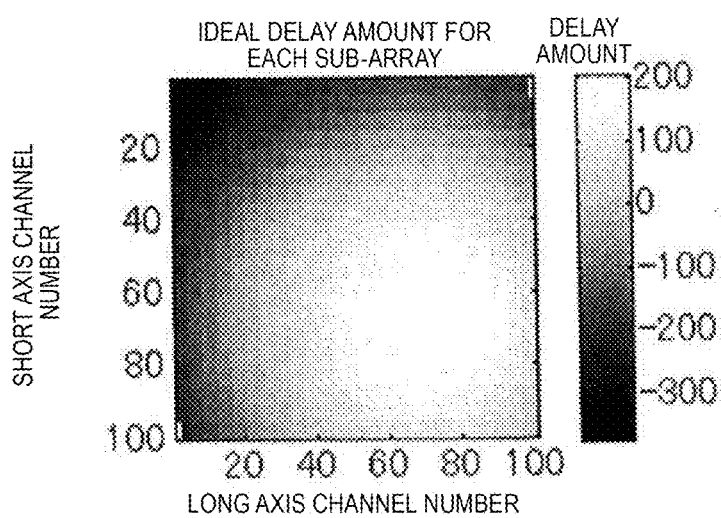
[Fig. 17B]
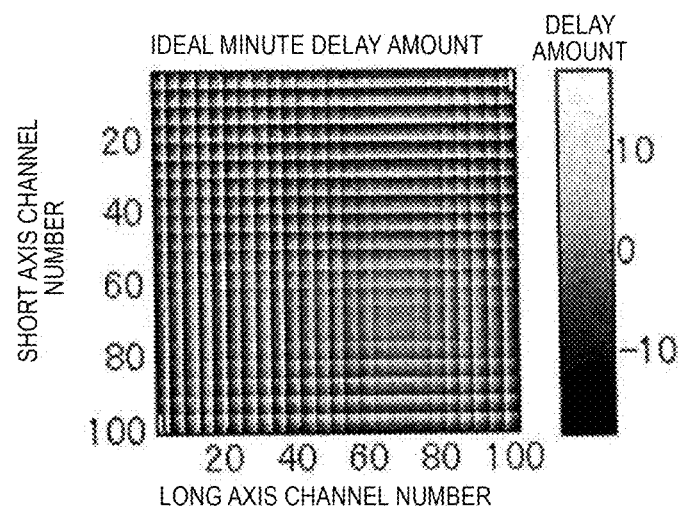
[Fig. 17C]

[Fig. 18A]
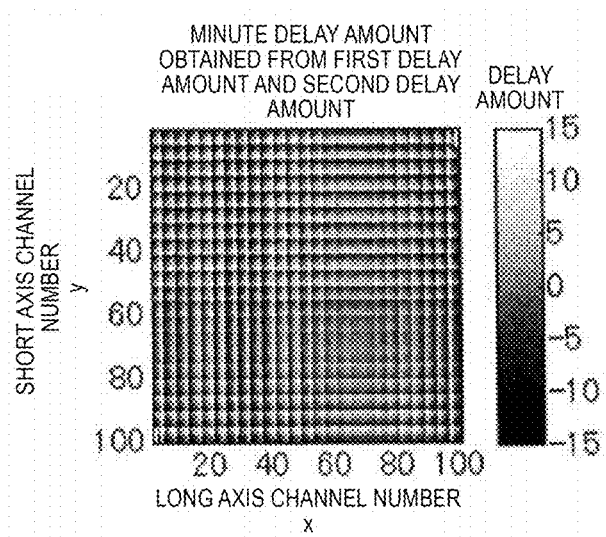
[Fig. 18B]
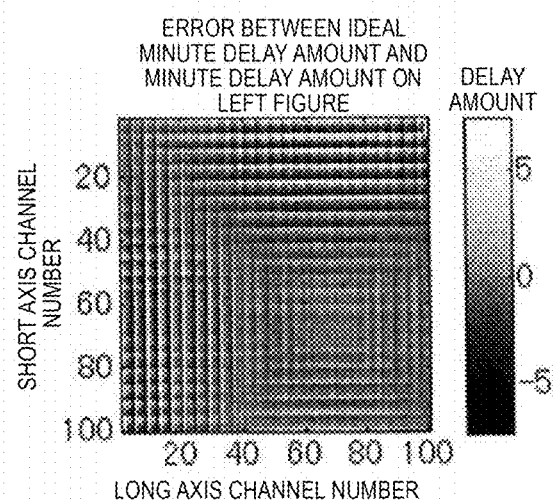
[Fig. 18C]
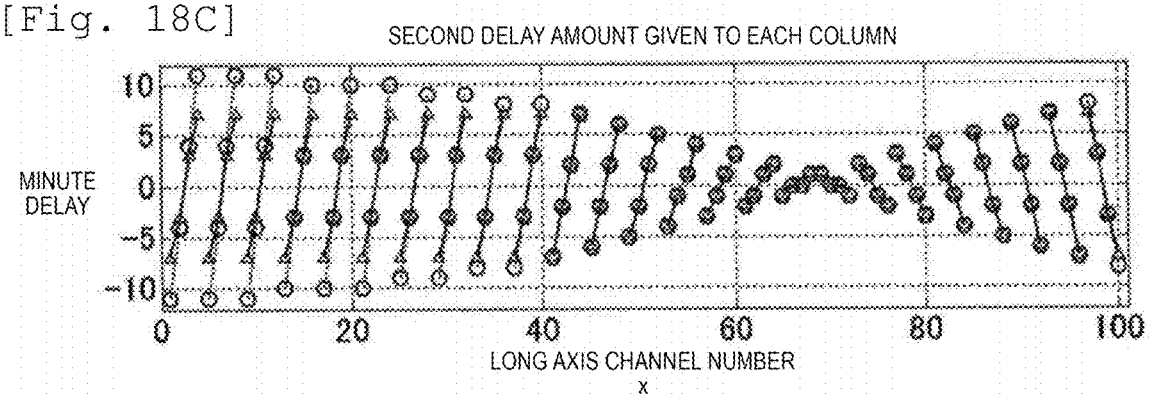
[Fig. 18D]
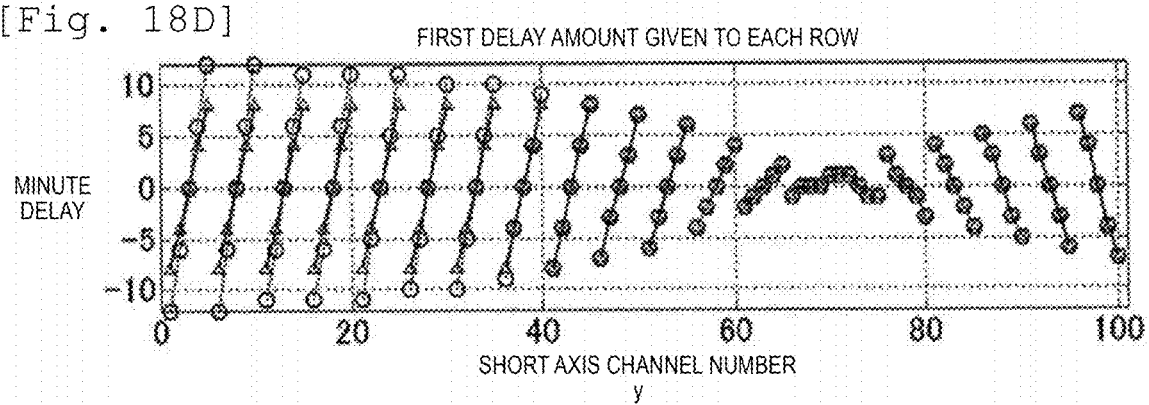

[Fig. 19]
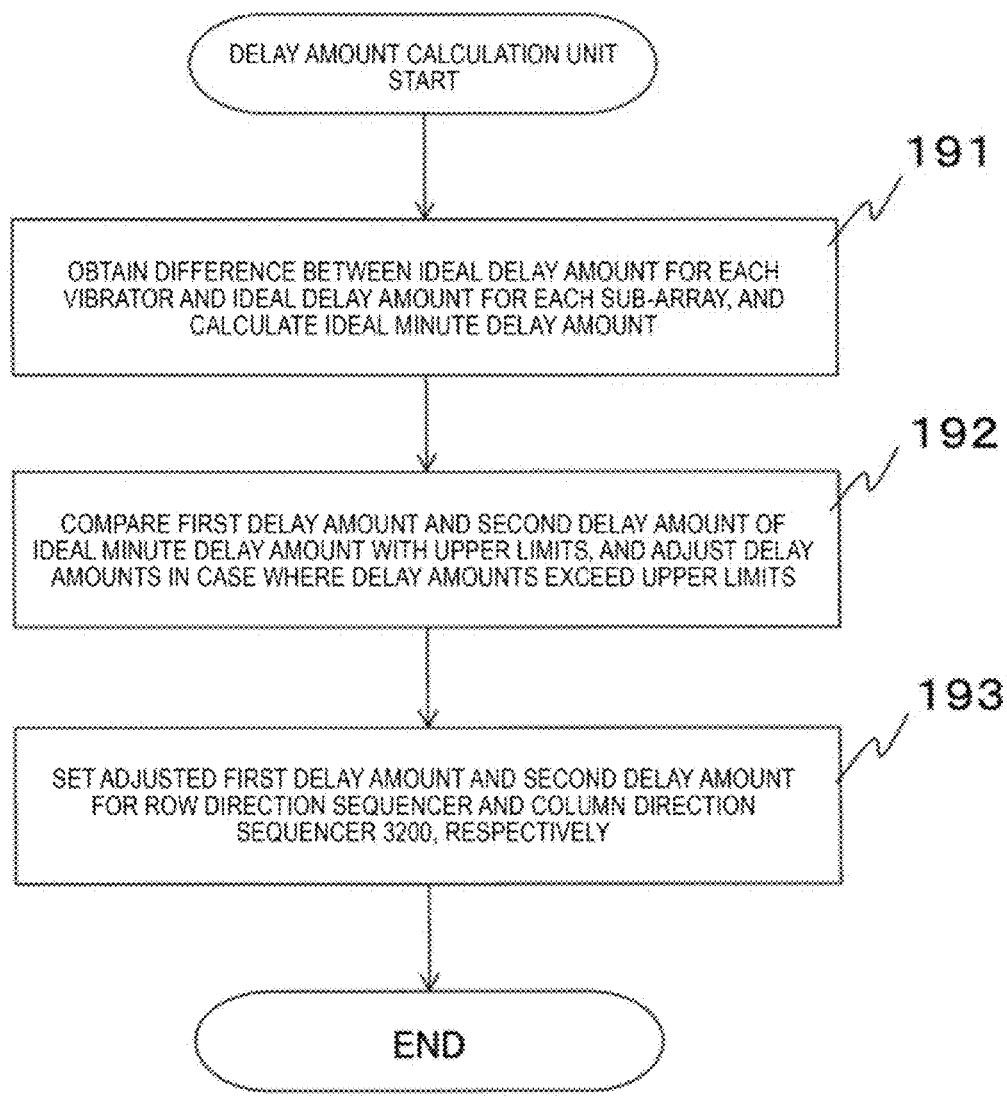

[Fig. 20A]
MINUTE DELAY AMOUNT OBTAINED FROM FIRST DELAY AMOUNT AND SECOND DELAY AMOUNT
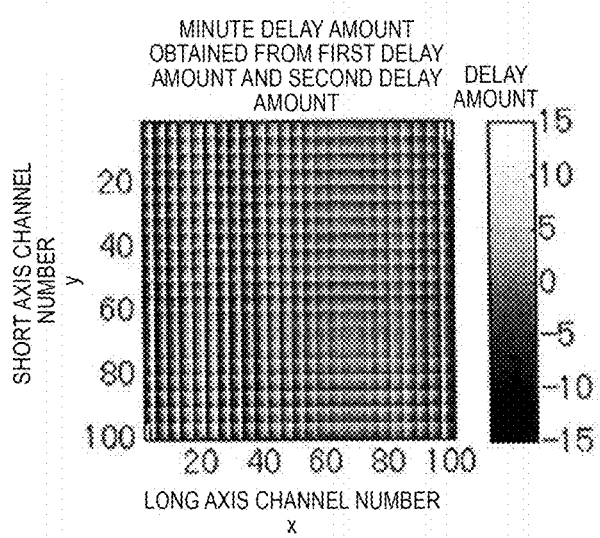
[Fig. 20B]
ERROR BETWEEN IDEAL MINUTE DELAY AMOUNT AND MINUTE DELAY AMOUNT ON LEFT FIGURE
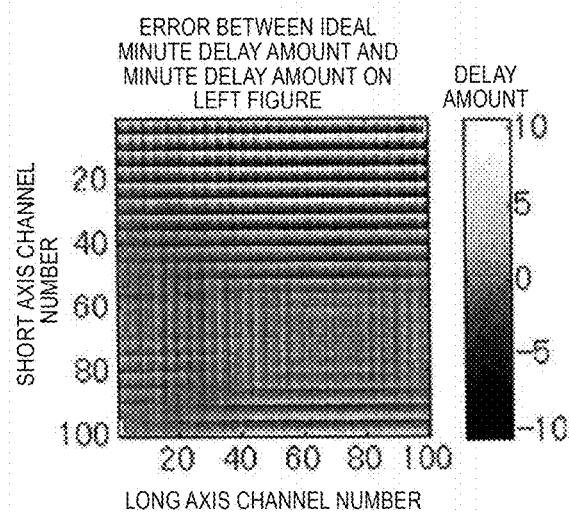
[Fig. 20C]
SECOND DELAY AMOUNT GIVEN TO EACH COLUMN
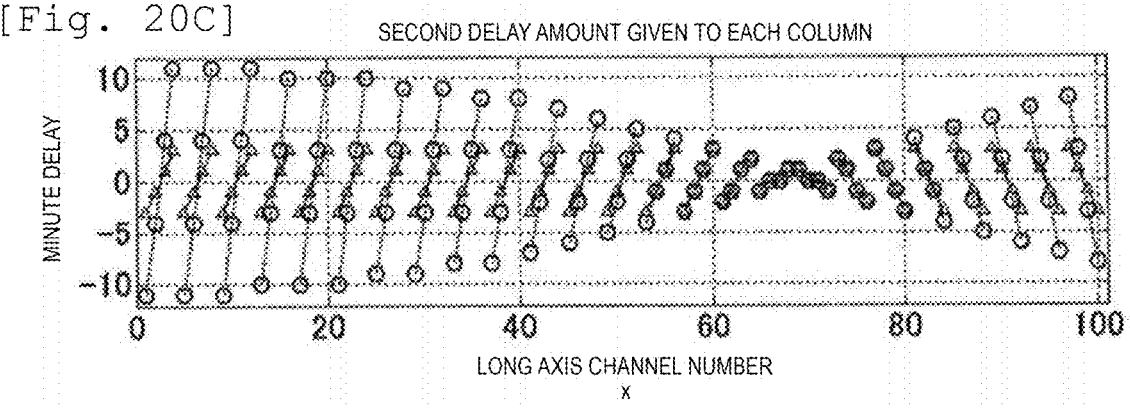
[Fig. 20D]
FIRST DELAY AMOUNT GIVEN TO EACH COLUMN
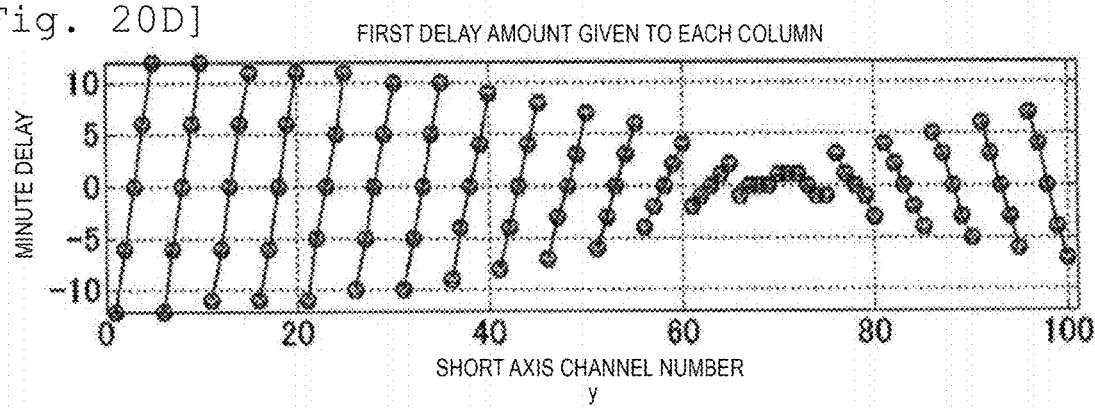

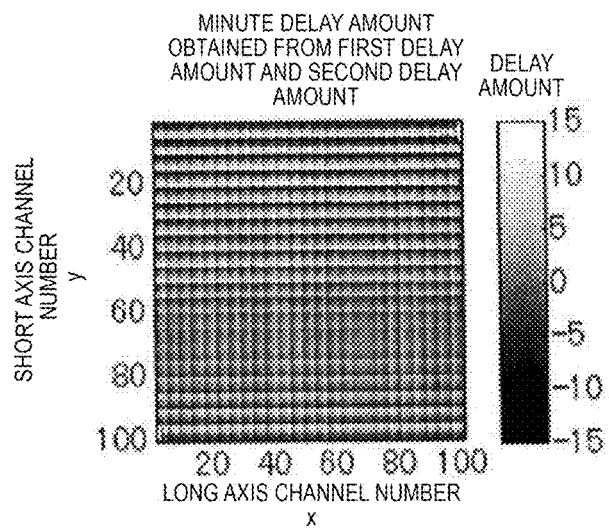
[Fig. 21A] MINUTE DELAY AMOUNT OBTAINED FROM FIRST DELAY AMOUNT AND SECOND DELAY AMOUNT
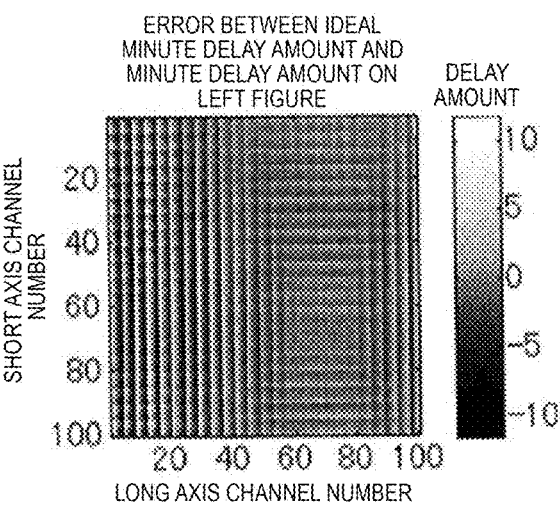
[Fig. 21B] ERROR BETWEEN IDEAL MINUTE DELAY AMOUNT AND MINUTE DELAY AMOUNT ON LEFT FIGURE
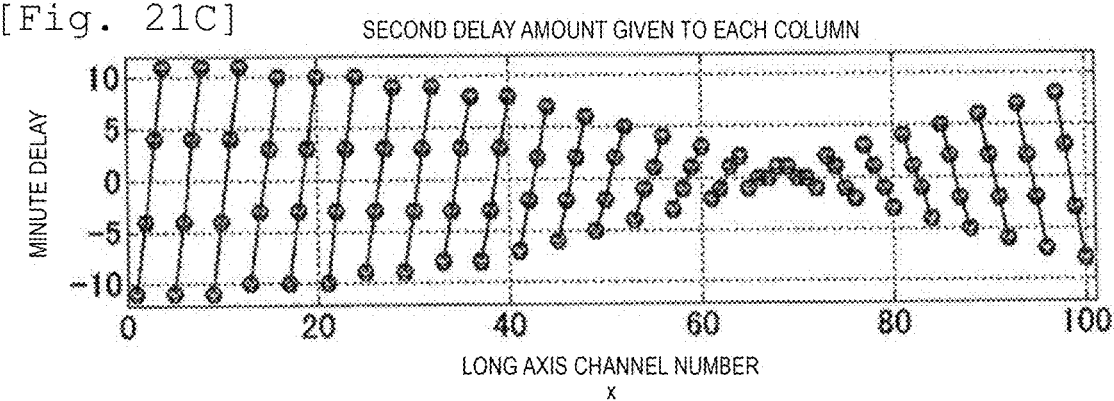
[Fig. 21C] SECOND DELAY AMOUNT GIVEN TO EACH COLUMN
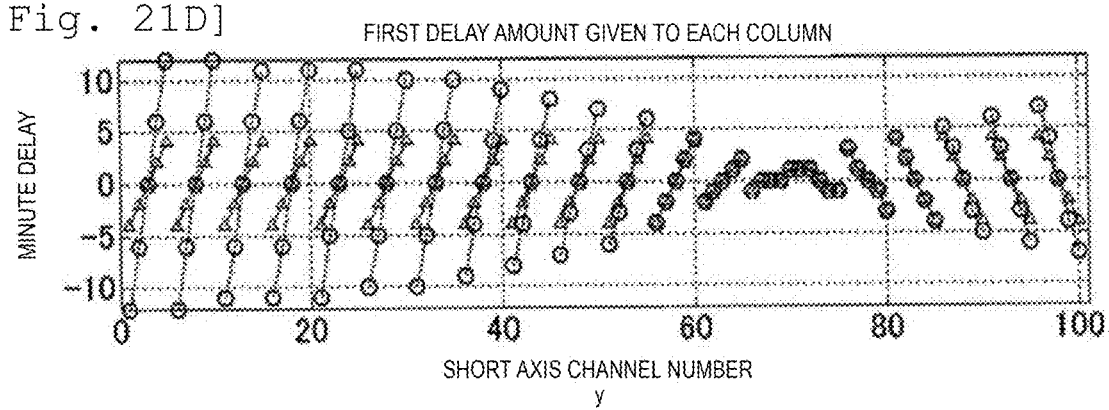
[Fig. 21D] FIRST DELAY AMOUNT GIVEN TO EACH COLUMN

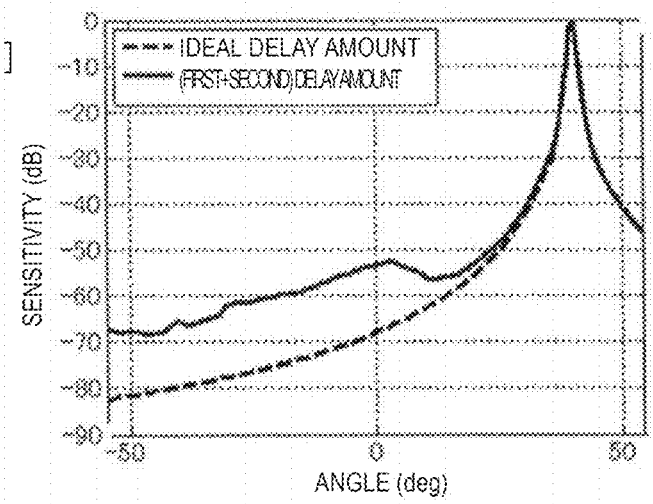
[Fig. 22A]
BALANCE TYPE
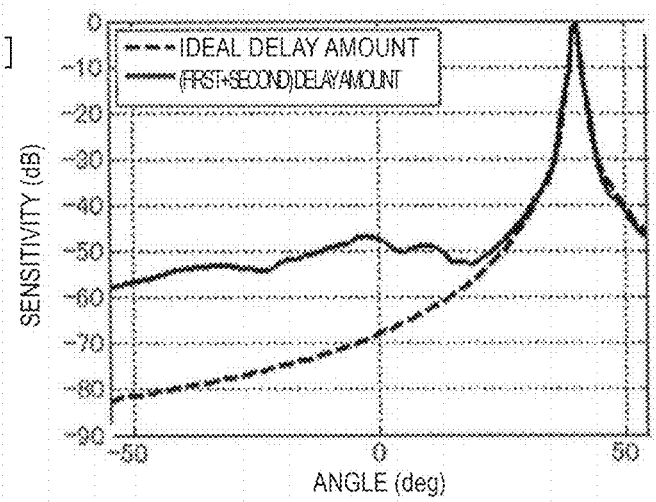
[Fig. 22B]
SECOND DELAY AMOUNT PRIORITY TYPE
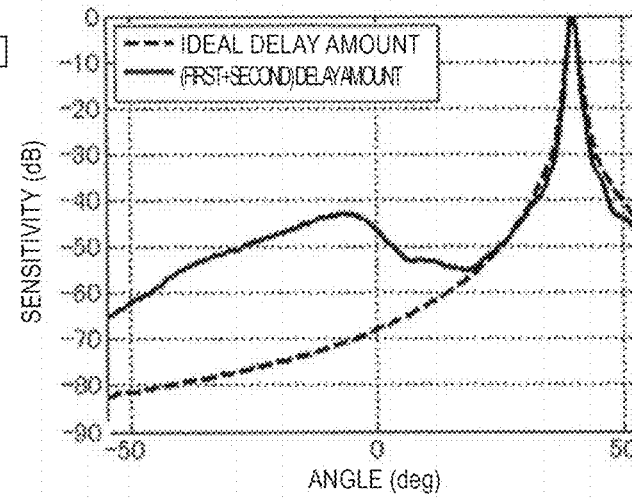
[Fig. 22C]
FIRST DELAY AMOUNT PRIORITY TYPE

[Fig. 23A]
BALANCE TYPE
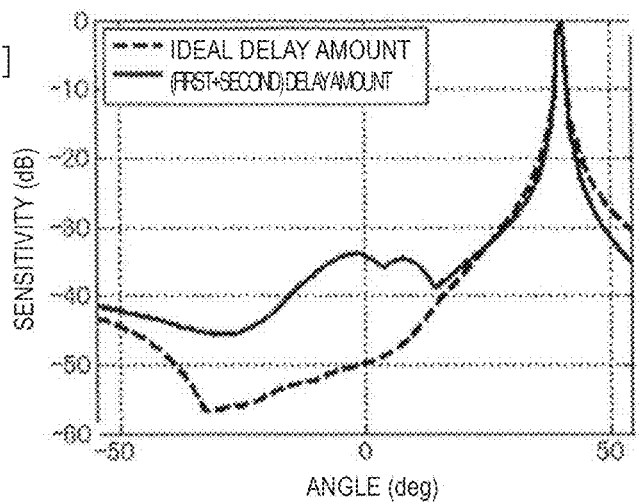
[Fig. 23B]
SECOND DELAY AMOUNT PRIORITY TYPE
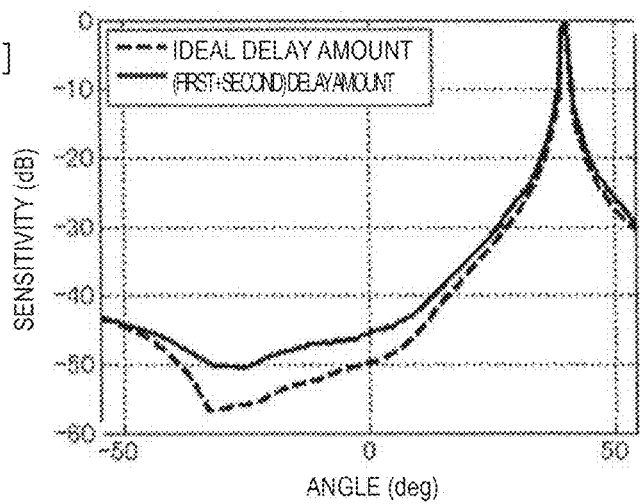
[Fig. 23C]
FIRST DELAY AMOUNT PRIORITY TYPE
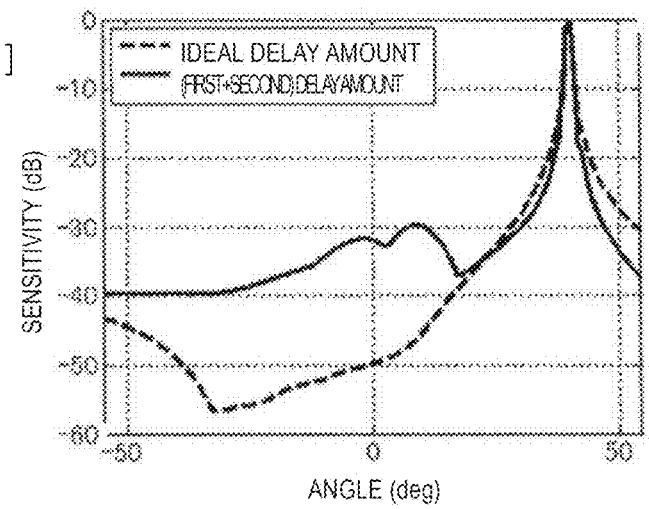

[Fig. 24A]
BALANCE TYPE
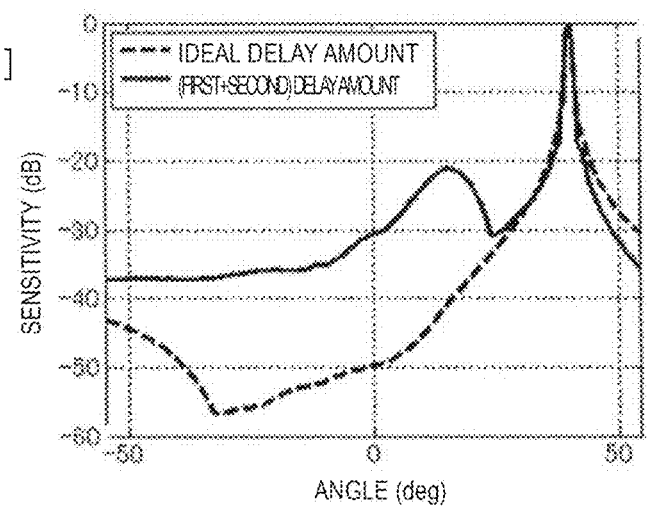
[Fig. 24B]
SECOND DELAY
AMOUNT PRIORITY
TYPE
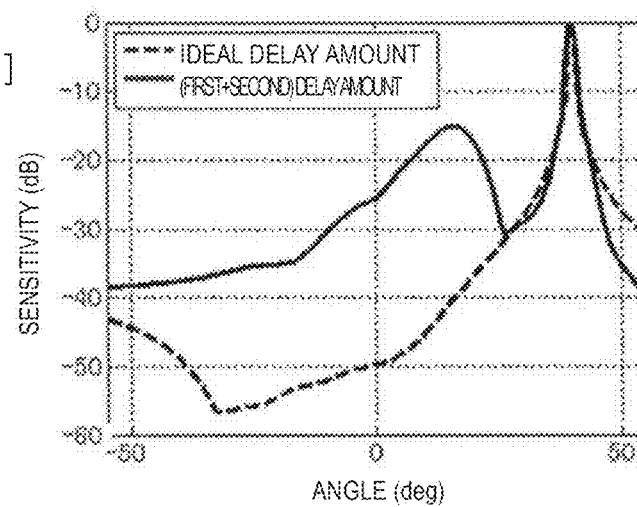
[Fig. 24C]
FIRST DELAY
AMOUNT PRIORITY
TYPE
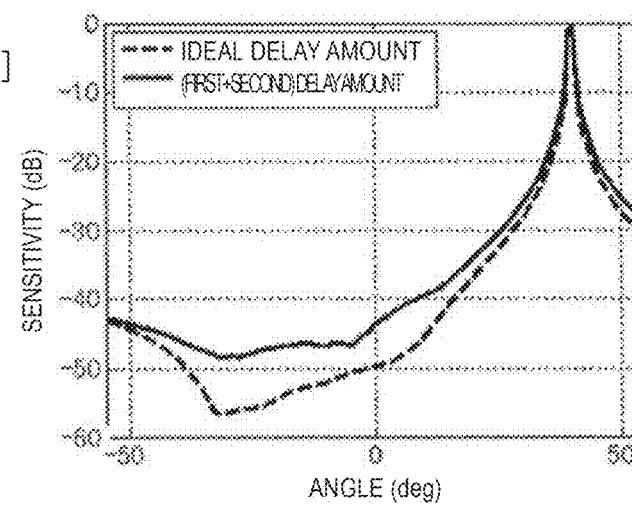

[Fig. 25A]
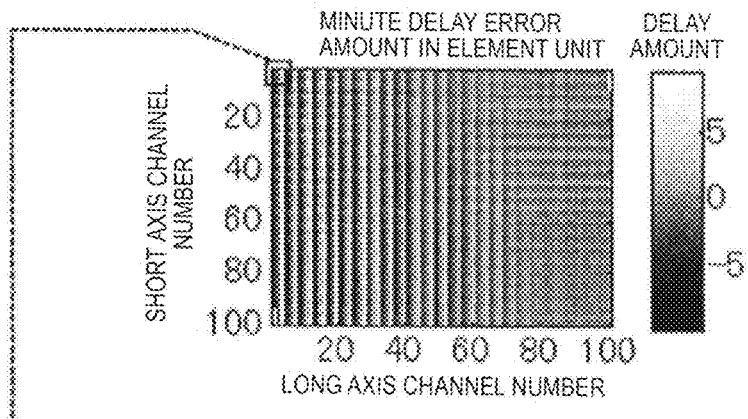
[Fig. 25B]
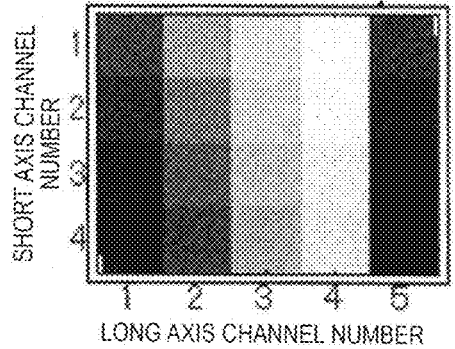
[Fig. 25C]
[Fig. 25D]
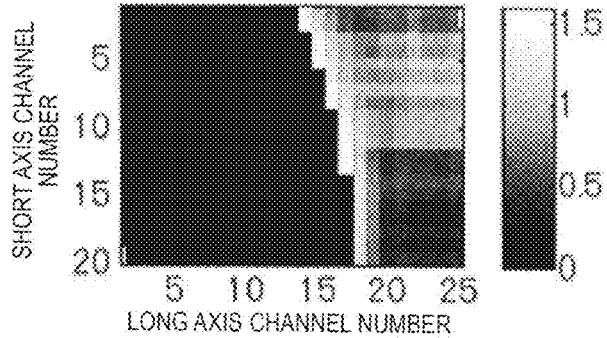

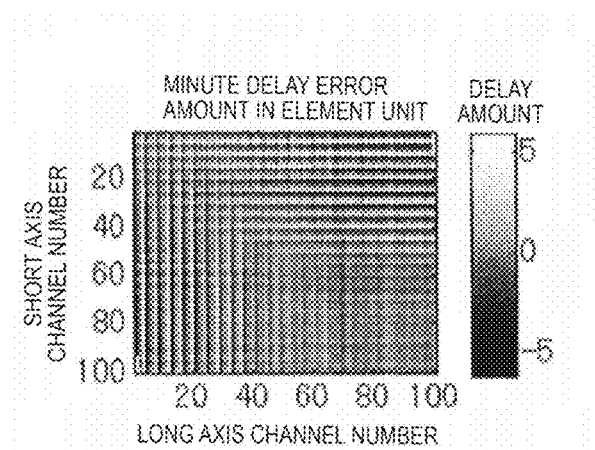
[Fig. 26A]
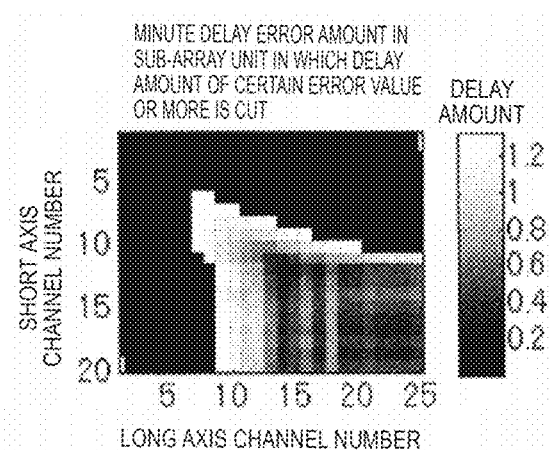
[Fig. 26B]
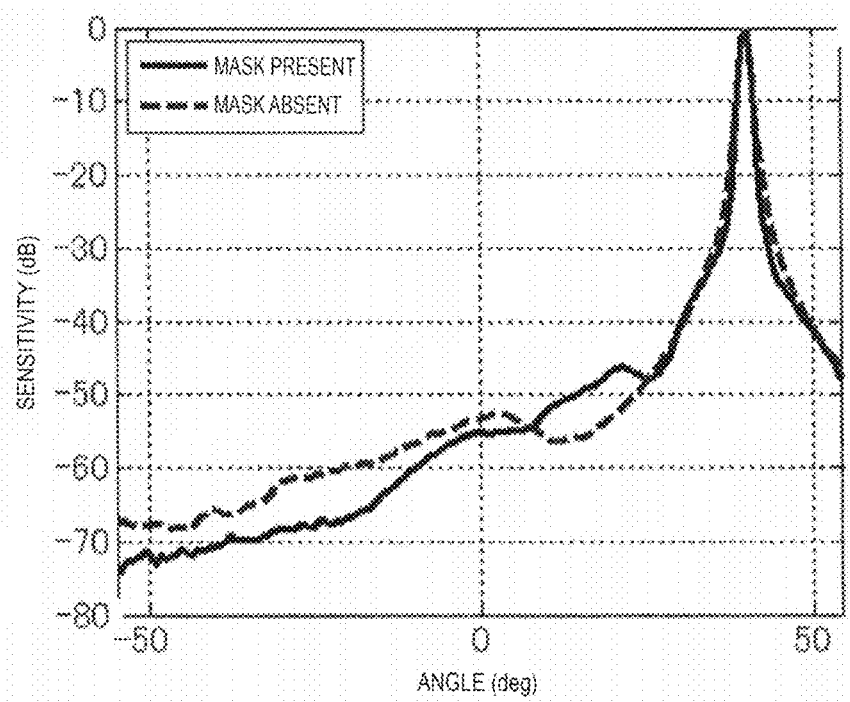
[Fig. 26C]

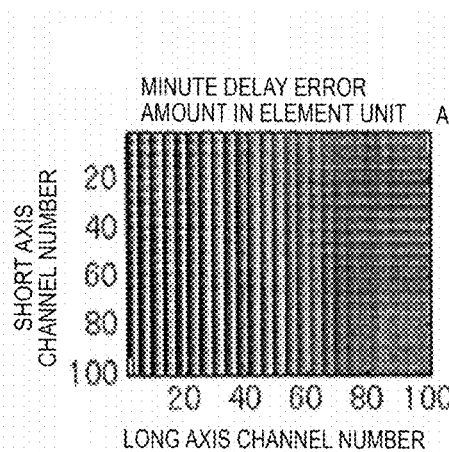
[Fig. 27A]
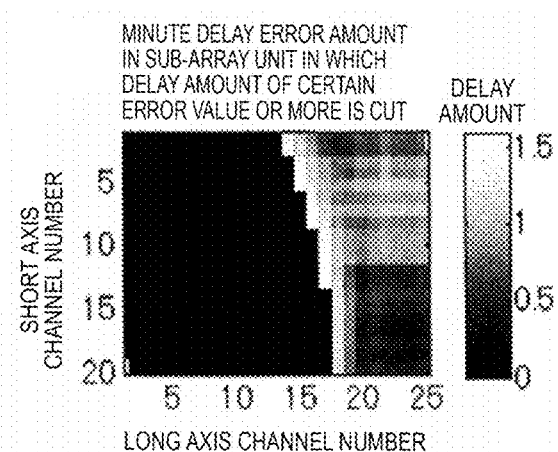
[Fig. 27B]
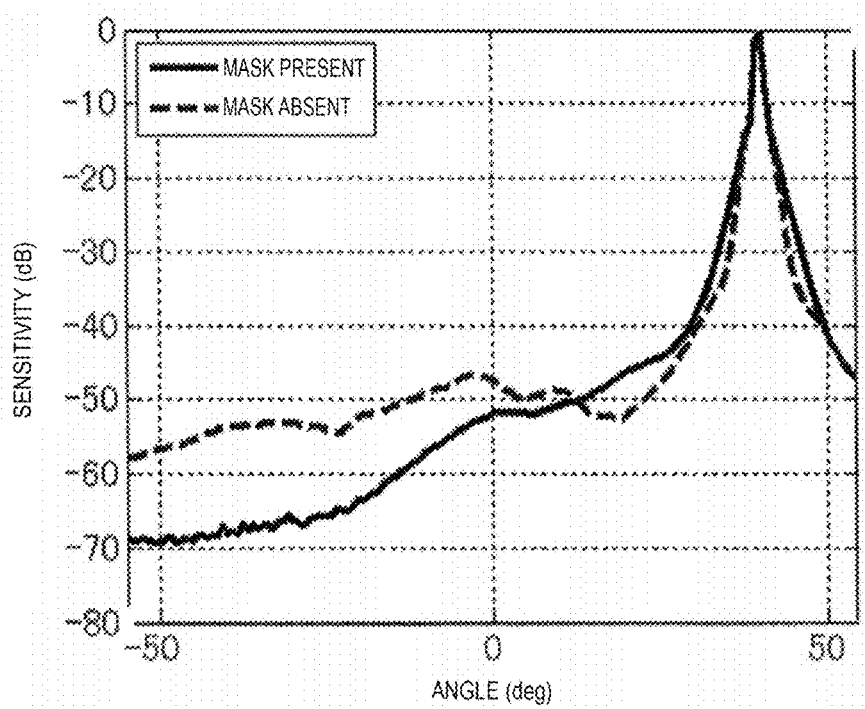
[Fig. 27C]

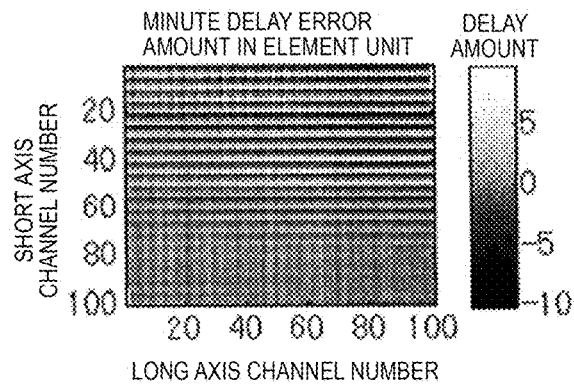
[Fig. 28A]
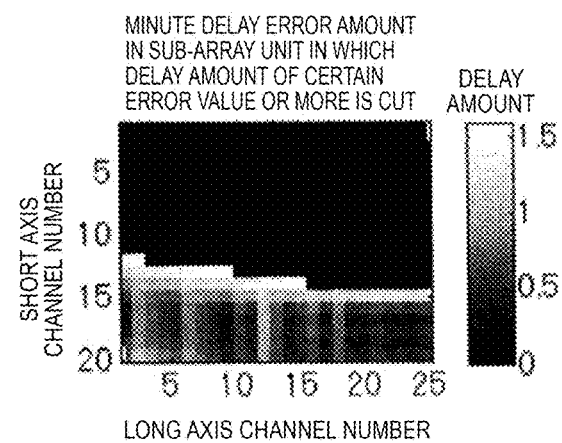
[Fig. 28B]
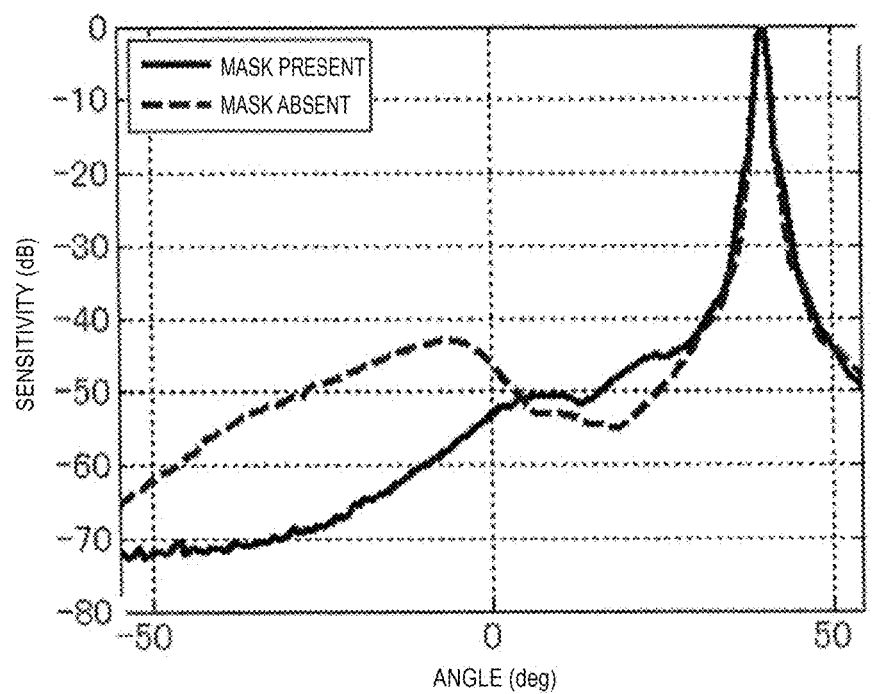
[Fig. 28C]

ULTRASONIC IMAGING DEVICE AND ULTRASONIC PROBE

TECHNICAL FIELD

The present invention relates to an ultrasonic imaging technique of capturing an image of the inside of a subject by transmitting ultrasonic waves to the subject from an ultrasonic probe and receiving ultrasonic waves reflected from the inside of the subject with the ultrasonic probe.

BACKGROUND ART

An ultrasonic imaging technique is a technique of capturing an image of the inside of a subject including a human body in a noninvasive manner by using an ultrasonic wave (a sonic wave not intended to be listened, and, generally, a sonic wave with a high frequency of 20 kHz or more). For example, a medical ultrasonic imaging apparatus transmits an ultrasonic beam into the body of a subject from an ultrasonic probe along a transmission scanning line, and receives an echo signal from the body inside. A reception beam former generates a signal obtained through phasing addition of received signals in a plurality of ultrasonic elements for each of a plurality of reception focal points on reception scanning lines. This phasing output is processed by an image processor, and thus an ultrasonic image is generated.

An ultrasonic probe has a plurality of ultrasonic vibrators (electroacoustic conversion elements) built thereinto, and performs transmission and reception of ultrasonic signals. The ultrasonic probe can generate an ultrasonic beam focused on a transmission focal point by applying an appropriate delay time to each element (channel) during transmission. A delay time applied to a received signal in each channel is changed, and delayed received signals are summed together, so that a signal focused on a desired reception focal point can be generated. Signals for the entire imaging region can be acquired by moving reception focal points, and an ultrasonic image is generated by using the signals. As mentioned above, a circuit performing a process of applying a delay time to each channel in order to focus on a certain point is called a beam former, a phasing circuit, or the like.

A configuration has been proposed in which a sub-array in which the number of channels is smaller than a total number of channel is set by collecting channels of a predetermined number in an ultrasonic probe, and an ultrasonic signal delay process is performed in two stages (PTL 1). In this technique, a plurality of sub-beam formers are disposed in an ultrasonic probe, and a main beam former is disposed in a main body. Each of the plurality of sub-beam formers delays and sums received signals in a plurality of channels of a corresponding sub-array, and sends a signal obtained through summing to the main beam former via a cable which connects the ultrasonic probe to the main body. The main beam former delays and sums signals received from the plurality of sub-beam formers so as to obtain a signal focused on a reception focal point. PTL 2 also discloses an apparatus including sub-beam formers and a main beam former.

PTL 3 discloses a circuit using sample-hold means and a plurality of capacitor memory circuits connected to thereto, as a circuit which delays an analog signal in a variable delay amount. Each of the capacitor memory circuits includes a capacitor, a write switch disposed in the previous stage of the capacitor, and a read switch disposed in the rear stage thereof. The plurality of capacitor memory circuits are connected in parallel to each other. The delay circuit can variably adjust a delay amount on the basis of a hold time in the sample-hold means, and differences between timings of write pulses and timings of read pulses for the plurality of capacitor memory circuits.

CITATION LIST

Patent Literature

PTL 1: JP-A-2005-270423
PTL 2: Specification of U.S. Pat. No. 6,013,032
PTL 3: JP-A-62-123819

SUMMARY OF INVENTION

Technical Problem

In order to generate an ultrasonic image having a high resolution in a short period of time, it is desirable to increase the number of ultrasonic vibrators forming an ultrasonic probe. For example, in a matrix array (two-dimensional array probe) in which ultrasonic vibrators are arranged in a two-dimensional manner, the number of channels is several thousands to about ten thousand. However, in order that the ultrasonic probe can be operated in a state of being held with the hand, there is a restriction in a thickness of a cable connecting the ultrasonic probe to a main body, and it is hard to directly connect thus all of several thousands to one thousand channels of the two-dimensional array probe to a main body apparatus unlike a one-dimensional array probe of the related art. Thus, as in PTLs 1 and 2, a configuration is desirable in which a plurality of sub-beam formers are disposed in an ultrasonic probe, and signals in a plurality of channels in a sub-array having undergone delay and summing process are delivered to a main beam former of a main body. Consequently, it is possible to reduce (channel reduction) the number of signal lines connected to the main beam former of the main body.

However, in the two-dimensional array probe having the number of channels of several thousands to ten thousand order, the number of sub-beam formers disposed in the ultrasonic probe increases, and thus it is difficult to dispose the sub-beam formers are in the two-dimensional array probe required to have a compact shape which fits in the palm of an examiner. Thus, it is desirable to realize a plurality of sub-beam formers with a semiconductor integrated circuit (IC) and with a small number of wiring layers (about four to eight layers).

A single sub-beam former includes at least delay circuits of the same number as the number of channels, a control circuit which sets a delay amount in each of the delay circuits, a signal line connecting each channel to the delay circuit, a signal line connecting the delay circuit to the control circuit, and a summing circuit which sums signals delayed by the delay circuits and outputs a signal obtained through summing. In a case where the delay circuit is configured to perform a time discrete charge storage region process using a capacitor (charge storage region), it is necessary to dispose about 16 to 64 capacitors in a delay circuit corresponding to a single channel in a case where a shallow part is desired to be imaged or in order to secure a delay time for which a range deviated in an angle relative to a direction directly under a probe can be imaged. A capacitor is formed according to a semiconductor process technique using, for example, a metal-insulator-metal (MIM) structure.

Each capacitor is required to be provided with a write switch, a read switch, and a signal line for controlling each switch. An IC in which such a plurality of delay circuits are separately controlled and integrated is a large-scale circuit, and is thus hard to realize with a die size of an IC chip which can be disposed in an ultrasonic probe.

Thus, development of an IC built-in circuit configuration which can control a plurality of sub-beam formers with as small a silicon area as possible is desirable.

An object of the present invention is to provide an ultrasonic imaging apparatus in which a sub-beam former IC which can control a plurality of capacitors (charge storage regions) of a delay circuit with a small number of signal lines is built into an ultrasonic probe.

Solution to Problem

According to the present invention, there is provided an ultrasonic imaging apparatus including an ultrasonic probe having a plurality of vibrators arranged in a two-dimensional manner, delay circuits respectively connected to the plurality of vibrators, and a beam former IC provided with a plurality of signal lines for setting delay amounts for the delay circuits, built thereinto; and a delay amount calculation unit that calculates delay amounts for the delay circuits according to a desired imaging direction. Each of the delay circuits is configured to allow a first delay amount and a second delay amount to be set for the delay circuit, and delays a signal by a delay amount obtained by adding the first delay amount and the second delay amount together. The plurality of delay circuits are divided into a plurality of groups, and are arranged in a row direction and a column direction so as to be mounted on the beam former IC for each of the groups. A common first delay amount is set for the delay circuits arranged in the same column in the group, and a common second delay amount is set for the delay circuits arranged in the same column in the group, by using signal lines. The delay amount calculation unit calculates the first delay amount and the second delay amount such that a sum of the first delay amount and the second delay amount set for each of the delay circuits is equal to or less than a predefined maximum delay amount.

Advantageous Effects of Invention

According to the present invention, there is provided a highly integrated control method in which delay circuits are arranged in a row direction and a column direction, a common first delay amount is set in the row direction, and a common second delay amount is set in the column direction, by using signal lines. Therefore, it is possible to control a set of delay amounts with a small number of signal lines and with high accuracy. It is possible to minimize image quality deterioration by setting a sum of the first delay amount and the second delay amount to be equal to or less than a predefined maximum delay amount.

BRIEF DESCRIPTION OF DRAWINGS

FIG. 1 is a perspective view of an ultrasonic imaging apparatus 1100 of an embodiment.

FIG. 2 is a block diagram of the ultrasonic imaging apparatus 1100 of the embodiment.

FIG. 3 is an explanatory diagram illustrating arrangement of delay circuits 5100 in a group (sub-beam former) 4000.

FIG. 4A is an explanatory diagram illustrating a delay amount during transmission for each vibrator of a vibrator array, FIG. 4B is an explanatory diagram illustrating a delay amount for a vibrator (delay circuit) of a single sub-array (sub-beam former), FIG. 4C is an explanatory diagram illustrating a delay amount of a transmission signal for each sub-beam former, and FIG. 4D is an explanatory diagram illustrating a delay amount (minute delay) during transmission for each delay circuit (vibrator) of a sub-beam former (sub-array).

FIG. 5 is a block diagram of the ultrasonic imaging apparatus 1100 of the embodiment.

FIG. 6A is an explanatory diagram illustrating a delay amount (minute delay) during reception for each delay circuit (vibrator) of a sub-beam former (sub-array), FIG. 6B is an explanatory diagram illustrating a delay amount in a vibrator (delay circuit) of a single sub-array (sub-beam former), FIG. 6C is an explanatory diagram illustrating a delay amount in a main beam former, and FIG. 6D is an explanatory diagram illustrating a delay amount during reception for each vibrator of a vibrator array.

FIG. 7 is an explanatory diagram illustrating that delay circuits 5100 in a group (sub-beam former) 4000 are connected to a summing unit.

FIG. 8 is a circuit diagram illustrating a circuit configuration of the delay circuit 5100.

FIG. 9 is a circuit diagram illustrating a circuit configuration of the sub-beam former 4000.

FIG. 10 is a circuit diagram illustrating a circuit configuration of a part of the sub-beam former 4000.

FIG. 11 is an explanatory diagram illustrating a delay amount set for each delay circuit 5100 of the sub-beam former 4000, a number $i_F$ of a capacitor on which writing is initially performed, and a number $j_F$ of a capacitor on which reading is initially performed.

FIG. 12A is an explanatory diagram illustrating a delay amount for each delay circuit of the sub-beam former 4000 in FIG. 11, and FIG. 12B is an explanatory diagram schematically illustrating a number $i_F$ of a capacitor on which writing is initially performed in each delay circuit of the sub-beam former 4000, and a number $j_F$ of a capacitor on which reading is initially performed.

FIG. 13 is a block diagram of an ultrasonic imaging apparatus 1100 of another aspect of the embodiment.

FIGS. 14A to 14D are explanatory diagrams illustrating a two-dimensional vibrator array 2100 and directions of an imaging range 6001.

FIGS. 15A to 15F are diagrams for explaining a relationship between the number of capacitors of three delay circuits arranged in a column direction and a delay amount.

FIG. 16 is a flowchart illustrating an operation of a maximum delay amount setting portion.

FIG. 17A is an explanatory diagram illustrating a distribution of an ideal delay amount in a vibrator, FIG. 17B is an explanatory diagram illustrating a distribution of an ideal delay amount for each sub-array, and FIG. 17C is an explanatory diagram illustrating a minute delay amount for a delay circuit of a sub-beam former.

FIG. 18A is an explanatory diagram illustrating a distribution of a set minute delay amount, FIG. 18B is an explanatory diagram illustrating an error between an ideal minute delay amount and the minute delay amount in FIG. 18A, and FIGS. 18C and 18D are graphs illustrating set values and ideal values of a second delay amount and a first delay amount.

FIG. 19 is a flowchart illustrating an operation of a delay amount calculation unit.

FIG. 20A is an explanatory diagram illustrating a distribution of a set minute delay amount, FIG. 20B is an explanatory diagram illustrating an error between an ideal minute delay amount and the minute delay amount in FIG. 20A, and FIGS. 20C and FIG. 20D are graphs illustrating set values and ideal values of a second delay amount and a first delay amount.

FIG. 21A is an explanatory diagram illustrating a distribution of a set minute delay amount, FIG. 21B is an explanatory diagram illustrating an error between an ideal minute delay amount and the minute delay amount in FIG. 21A, and FIGS. 21C and 21D are graphs illustrating set values and ideal values of a second delay amount and a first delay amount.

FIGS. 22A to 22C are graphs illustrating beam profiles in a case where set values of the second delay amount and the first delay amount are different from each other in the same imaging direction.

FIGS. 23A to 23C are graphs illustrating beam profiles in a case where set values of the second delay amount and the first delay amount are different from each other in the same imaging direction.

FIGS. 24A to 24C are graphs illustrating beam profiles in a case where set values of the second delay amount and the first delay amount are different from each other in the same imaging direction.

FIGS. 25A to 25D are explanatory diagrams illustrating procedures from a minute delay error amount in a vibrator to sub-mask processing.

FIGS. 26A and 26B are explanatory diagrams illustrating a minute delay error amount in a vibrator and sub-mask processing, and FIG. 26C is a graph illustrating a beam profile.

FIGS. 27A and 27B are explanatory diagrams illustrating a minute delay error amount in a vibrator and sub-mask processing, and FIG. 27C is a graph illustrating a beam profile.

FIGS. 28A and 28B are explanatory diagrams illustrating a minute delay error amount in a vibrator and sub-mask processing, and FIG. 28C is a graph illustrating a beam profile.

DESCRIPTION OF EMBODIMENTS

An embodiment of the present invention will be described.

An ultrasonic imaging apparatus of the embodiment of the present invention will be described.

As illustrated in FIG. 1, an ultrasonic imaging apparatus 1100 of the embodiment includes an ultrasonic probe 1000 and a main body 1110. As illustrated in FIG. 2, the ultrasonic probe 1000 includes a vibrator array 2100 and an in-probe beam former IC 2000. The vibrator array 2100 has a configuration in which a plurality of vibrators 2111 are arranged in a two-dimensional manner. The in-probe beam former IC 2000 includes delay circuits 5100 respectively connected to the plurality of vibrators 2111, and a plurality of signal lines 3210 and 3310 for setting delay amounts for the delay circuits 5100. The ultrasonic imaging apparatus 1100 includes a delay amount calculation unit 200 which calculates delay amounts set for the delay circuits 5100 according to a desired imaging direction. FIG. 2 illustrates a structure in which the delay amount calculation unit 200 is mounted on the main body 1110, but the delay amount calculation unit 200 may be mounted on the ultrasonic probe 1000.

Each of the delay circuits 5100 allows a first delay amount and a second delay amount to be set therefor, and delays a signal by a delay amount obtained by adding the first delay amount to the second delay amount. A detailed structure of the delay circuit 5100 will be described later.

The plurality of delay circuits 5100 are divided into a plurality of groups 4000 as illustrated in FIG. 2. The plurality of delay circuits 5100 are arranged in a row direction and a column direction in each group 4000, and are mounted on the beam former IC 2000. The common first delay amount is set for the delay circuits 5100 arranged in the same row in the group 4000 via the signal line 3310. The common second delay amount is set for the delay circuits 5100 arranged in the same column in the group 4000 via the signal line 3210.

The delay amount calculation unit 200 calculates the first delay amount and the second delay amount such that a sum of the first delay amount and the second delay amount set for the delay circuit 5100 is the maximum delay amount set in advance. Hereinafter, the signal line 3310 will be referred to as a first signal line, and the signal line 3210 will be referred to as a second signal line.

In addition to the plurality of delay circuits 5100, a column direction delay sequencer 3200 and a row direction delay sequencer 3300 are integrated into the in-probe beam former IC 2000. In addition to the first signal lines 3310 and the second signal lines 3210, vibrator wires 5310 respectively connecting the plurality of vibrators 2111 to the delay circuits 5100 are integrated into the in-probe beam former IC 2000. The delay circuits 5100 forming the in-probe beam former IC 2000 are provided on a one-to-one basis for any one of the vibrators 2111 and the vibrator wires 5310 via an intermediate analog signal circuit group, and delay transmission signals delivered to the vibrators 2111 and reception signals received in the vibrators 2111 during reception of ultrasonic waves.

The delay circuit 5100 can set the first delay amount and the second delay amount, and delays a transmission signal and a reception signal by a delay amount obtained by adding the first delay amount to the second delay amount.

As illustrated in FIG. 2, in a signal processing circuit group including a plurality of delay circuits 5100 correlated with the vibrators 2111 on a one-to-one basis, the plurality of delay circuits 5100 are divided into sets (groups 4000) collected in a lattice arrangement form, and are integrated into the in-probe beam former IC 2000 so as to be arranged in the row direction (transverse direction) and the column direction (longitudinal direction). The sets (groups 4000) of collecting the plurality of delay circuits 5100 in a lattice arrangement form are regarded as a partial beam former which can form beam directivity in transmission and reception due to delay as the whole of the sets (the whole of the plurality of groups 4000). Therefore, in the following description, the groups 4000 will be referred to as sub-beam formers 4000.

As described above, delay amounts are set for the delay circuits 5100 of a single sub-beam former 4000 via the first signal line 3310 in each row of the delay circuits 5100 and via the second signal line 3210 in each column. In other words, the common first delay amount is set for the delay circuits 5100 arranged in the same row via the first signal line 3310. The common second delay amount is set for the delay circuits 5100 arranged in the same column via the second signal line 3210. Each delay circuit 5100 delays a signal by a delay amount obtained by adding the set first delay amount and second delay amount together. The first signal lines 3310 and the second signal lines 3210 are respectively connected to the row direction sequencer 3300 and the column direction sequencer 3200, and signals for setting delay amounts are delivered via the signal lines.

As mentioned above, there is provided a configuration in which the delay circuits 5100 disposed for the vibrators 2111 are divided into a plurality of sub-beam formers 4000, and are arranged in the row direction and the column direction, and the common delay amount is set in each row and each column, and thus the signal lines may be disposed for each row and each column. Thus, delay amounts can be set with a smaller number of signal lines than in a case where a signal line is separately disposed for each delay circuit 5100. Since the delay circuit 5100 delays a signal by a delay amount obtained by adding the first delay amount to the second delay amount, a delay amount can be set through a combination of the first delay amount and the second delay amount, and thus a larger number of delay amounts can be set through combination with a small number of signal lines.

Describing again an arrangement relationship of the delay circuits 5100 of the sub-beam former 4000 with reference to FIG. 3, the first signal line 3310 in the row direction is disposed in each row in the group. The first signal line 3310 is connected in common to the delay circuits 5100 arranged in the row, and is used to set the first delay amount. The second signal line 3210 in the column direction is disposed in each column in the group. The second signal line 3210 is connected in common to the delay circuits 5100 arranged in the column, and is used to set the second delay amount. In FIGS. 2 and 3, the signal lines are indicated by four horizontal lines (solid lines) and three vertical lines (dashed lines), but each thereof indicates a signal bus connection, and may be mounted with a wiring of a plurality of lines in an embodiment circuit. The row direction sequencer 3300 and the column direction sequencer 3200 are not necessarily integrated into the same die, chip, or device as that of the in-probe beam former IC 2000, and may be built into the ultrasonic probe 1000 separately from the in-probe beam former IC 2000.

Arrangements of the delay circuits 5100 in the row direction and the column direction in the sub-beam former 4000 preferably correspond to two-dimensional arrangements of the vibrators 2111 connected to the delay circuits 5100. A set of the vibrators 2111 connected to the delay circuits 5100 forming a single sub-beam former 4000 will be referred to as a sub-array 2110 in the following description. In an array (vibrator array 2100) of the two-dimensionally arranged vibrators 2111, a large delay amount is set for a vibrator which is closest to a transmission focal point among the plurality of vibrators 2111, a small delay amount is set for a vibrator which is farthest from the transmission focal point, and a delay amount is set for vibrators located in the region therebetween so as to be gradually in an annular shape. Thus, in a case where transmission is performed in a direction directly under the vibrator array 2100 (a normal direction to the vibrator array 2100 from the center of the vibrator array 2100), a delay amount as illustrated in FIG. 4(a) is obtained. Delay amounts for a plurality of vibrators 2111 of the single sub-array 2110 gradually change from the vibrator 2111 at a single end toward the vibrators 2111 diagonally disposed therefrom as illustrated in FIG. 4(b). As mentioned above, a distribution in which Delay amounts for a plurality of vibrators 2111 of the single sub-array 2110 change from the vibrator 2111 at a single end toward the vibrators 2111 diagonally disposed therefrom can be set by a configuration in which a delay amount common to each row and a delay amount common to each column in the sub-beam former 4000 are set, and both of the delay amounts are added together. If either of a delay amount common to each row and a delay amount common to each column is made constant, a distribution in which a delay changes in the column direction or the row direction can be set. Therefore, the arrangement of the delay circuits 5100 of the sub-beam former 4000 preferably corresponds to the two-dimensional arrangement (sub-array 2110) of the vibrators 2111 connected to the delay circuits 5100.

In FIGS. 2 and 4(b), for convenience of illustration, the number of the vibrators 2111 of the vibrator array 2100 is illustrated to be smaller than that in FIG. 4(a). In FIG. 2, lines indicating that some signal lines of a plurality of sub-beam formers 4000 are connected to the row direction sequencer 3300 or the column direction sequencer 3200 are omitted.

In FIG. 2, a plurality of sub-beam formers 4000 are mounted on the in-probe beam former IC 2000 with an interval, but arrangement of the sub-beam formers 4000 on the in-probe beam former IC 2000 is not limited to the arrangement illustrated in FIG. 2, and the sub-beam formers 4000 adjacent to each other may be continuously disposed. In this case, the signal lines 3310 and 3210 may be wired over or under another sub-beam former 4000 so as to be connected to the row direction sequencer 3300 and the column direction sequencer 3200. As will be described later, signal lines of the adjacent sub-beam formers 4000 may be connected to each other. Herein, a description will be made of a case of a configuration in which signal lines of the adjacent sub-beam formers 4000 are not connected to each other, and are directly connected to the row direction sequencer 3300 and the column direction sequencer 3200.

Transmission Beam Forming

In the present embodiment, a transmission signal generation unit 3100 is disposed inside the ultrasonic probe 1000 as illustrated in FIGS. 2 and 5.

As illustrated in FIG. 4(c), the transmission signal generation unit 3100 receives a delay amount in the unit of the sub-beam former 4000 (the unit of the sub-array 2110), corresponding to a distance from the transmission focal point to the sub-array 2110, from the delay amount calculation unit 200 of the main body 1010 so as to generate a transmission signal, and delivers the transmission signal to each sub-beam former 4000 as illustrated in FIG. 5. A delay amount in the unit of the sub-beam former 4000 (the unit of the sub-array 2110) corresponds to a distance between a certain point (for example, the center) of the sub-array 2110 and the transmission focal point. In other words, at this time, a delay amount of a transmission signal in the same sub-beam former 4000 (the same sub-array 2110) is constant.

On the other hand, the column direction sequencer 3200 and the row direction sequencer 3300 receive a delay amount (FIG. 4(d)) obtained by subtracting a delay amount (FIG. 4(c)) in the unit of the sub-array 2110 (sub-beam former 4000) from the delay amount (FIG. 4(a)) for each vibrator 2111 corresponding to the distance from the transmission focal point, from the delay amount calculation unit 200, and generates a signal to be set for each delay circuits 5100. The generated delay amount (FIG. 4(d)) is set for each delay circuit 5100 of each sub-beam former 4000. The delay amount in FIG. 4(d) is a delay amount is a delay amount which changes from the vibrator 2111 at a single end to the vibrators 2111 diagonally disposed therefrom, or changes in the row direction or the column direction.

Each delay circuit 5100 forming the sub-beam former 4000 delays the transmission signal (FIG. 4(c)) including the delay amount for each sub-array 2110, received from the transmission signal generation unit 3100, by the delay amount in FIG. 4(d), and delivers the signal to each vibrator 2111. Consequently, as illustrated in FIG. 4(a), a distribution of the delay amounts of the transmission signals received by the respective vibrators 2111 is a distribution corresponding to distances between the respective vibrators and the transmission focal point. Therefore, it is possible to transmit an ultrasonic beam having a predetermined transmission focal point from the vibrator array 2100.

As mentioned above, the transmission signal generation unit 3100 disposed in the ultrasonic probe 1000 generates a transmission signal which is delayed according to a focal point during transmission for each sub-beam former 4000 (sub-array 2110) in advance, and thus each of a plurality of delay circuits 5100 forming the sub-beam former 4000 may delay a transmission signal by a minute delay amount as illustrated in FIG. 4(d), and a dynamic range of a delay amount for the delay circuit 5100 can be reduced.

In this configuration, a transmission signal can be generated in the ultrasonic probe 1000, and thus it is not necessary to generate a transmission signal in the main body 1110 and transmit the transmission signal to the ultrasonic probe 1000 via a cable 1010. Therefore, it is possible to achieve a small scale of the cable 1010 and to prevent noise from being mixed with a transmission signal in the cable 1010.

Reception Beam Forming

An ultrasonic beam transmitted to the inside of an imaging target 1300 from the vibrator 2111 reaches the vibrator 2111 again through reflection or scattering, and is received by the vibrator 2111. The vibrator 2111 converts the received ultrasonic wave into an electrical signal (reception signal), and delivers the signal to the delay circuit 5100 connected to each vibrator 2111.

In a case where a reception focal point is set in a direction directly under (normal line) the vibrator array 2100, the column direction sequencer 3200 and the row direction sequencer 3300 generate delay amounts in FIG. 6(a), and set the delay amounts for the respective delay circuits 5100 of the sub-beam former 4000. Each of the delay amounts in FIG. 6(a) is a delay amount obtained by subtracting a delay amount (FIG. 6(c)) corresponding to a distance between the reception focal point and a certain point (for example, the center) of the sub-array 2110 from a delay amount (refer to FIG. 6(d)) corresponding to a distance between the reception focal point and the vibrator 2111, and is generated according to the reception focal point by the delay amount calculation unit 200 so as to be set for the row direction sequencer 3300 and the column direction sequencer 3200. Consequently, the delay circuit 5100 of each sub-beam former 4000 (sub-array 2110) delays a reception signal by a set delay amount, that is, a delay amount corresponding to a predetermined reception focal point as illustrated in FIG. 6(a). The delay amount in FIG. 6(a) is a delay amount is a delay amount which changes from the vibrator 2111 at a single end to the vibrators 2111 diagonally disposed therefrom, or changes in the row direction or the column direction, as illustrated in FIG. 6(b) in terms of each sub-beam former 4000 (sub-array 2110).

As illustrated in FIG. 7, a summing unit 3400 is mounted for each sub-beam former 4000 on the in-probe beam former IC 2000, and reception signals delayed by the plurality of delay circuits 5100 forming the sub-beam former 4000 are summed together in the summing unit 3400 disposed for each sub-beam former 4000. Consequently, it is possible to obtain a phasing addition signal as a result of phasing addition of reception signals in a plurality of vibrators 2111 of a single sub-array 2110 corresponding to the sub-beam former 4000 for a predetermined reception focal point. The sub-beam former 4000 corresponding to the sub-array 2110 outputs the phasing addition signal to the main body 1110 via the cable 1010.

As illustrated in FIG. 2, a main beam former 210 is disposed in the main body 1110. As illustrated in FIG. 6(c), the main beam former 210 receives a delay amount corresponding to a distance between a certain point (for example, the center) of the sub-array 2110 and the reception focal point from the delay amount calculation unit 200, and further delays the phasing addition signal for each sub-array 2110 (sub-beam former 4000). Consequently, as illustrated in FIG. 6(d), it is possible to obtain the same delay amount for each vibrator 2111 as in a case where a reception signal in the vibrator 2111 is delayed according to a distance between the vibrator 2111 and the reception focal point.

Therefore, an image generation unit 260 of the main body 1110 can obtain respective phasing addition signals for a plurality of reception focal points at different positions, and can generate an ultrasonic image of the inside of a subject by performing signal processing as necessary.

Configuration of Delay Circuit

Next, a description will be made of a configuration of the delay circuit 5100. As illustrated in FIG. 8, a single delay circuit 5100 includes K capacitors 51 connected in parallel to each other, and a first switch 52 and a second switch 53 respectively disposed at one side and the other side of each capacitor 51 in the K capacitors 51. For convenience of illustration, FIG. 8 illustrates an example of a case where K is 5, but, actually, a value of K is set according to necessary delay amounts. For example, the capacitors 51 of a predetermined number within a range of K=16 to 64 are connected in parallel to each other. Therefore, K capacitors 51-1 to 51-K, first switches 52-1 to 52-K, and second switches 53-1 to 53-K are disposed in a single delay circuit 5100.

The single delay circuit 5100 is connected to the first signal lines 3310 formed of K signal lines 33-1 to 33-K of the same number as the number of the capacitors 51 and the second signal lines 3210 formed of K signal lines 32-1 to 32-K. The K first signal lines 3310 (signal lines 33-1 to 33-K) are respectively connected to the K first switches 52-1 to 52-K. The K second signal lines 3210 (signal lines 32-1 to 32-K) are respectively connected to the K second switches 53-1 to 53-K. Specifically, among the K first signal lines 3310, the i-th (where i is an integer of 1≤i≤K) signal line 33-$i$ is connected to the first switch 52-$i$ of the i-th capacitor 51-$i$ among the capacitors 51 connected in parallel to each other, and is used to control opening and closing thereof. Similarly, among the K second signal lines 3210, the j-th (where j is an integer of 1≤j≤K) signal line 32-$j$ is connected to the second switch 53-$j$ of the j-th capacitor 51-$j$ among the capacitors 51 connected in parallel to each other, and is used to control opening and closing thereof.

An input switching unit 54 which inputs a signal to be delayed is disposed on the first switches 52 of the capacitors 51 connected in parallel to each other. The input switching unit 54 is connected to the transmission signal generation unit 3100 and the vibrators 2111. During transmission, the input switching unit 54 selects the transmission signal generation unit 3100 so as to input a transmission signal to the delay circuit 5100. During reception, the vibrator 2111 is selected, and a reception signal is input to the delay circuit 5100.

An output switching unit 55 which selects a delivery destination of a delayed output is disposed on the second switches 53 of the capacitors 51 connected in parallel to each other. The output switching unit 55 is connected to the vibrators 2111 and the summing unit 3400. During transmission, the output switching unit 55 selects the vibrator 2111 so as to output a transmission signal delayed by the delay circuit 5100 to the vibrator 2111. During reception, the summing unit 3400 is selected, and thus a reception signal delayed by the delay circuit 5100 is output to the summing unit 3400.

For example, in a case where the n (=3) delay circuits 5100 are arranged in the row direction, and the m (=4) delay circuits 5100 are arranged in the column direction, the sub-beam former 4000 (refer to FIGS. 2 and 3) has a configuration as illustrated in FIG. 9. FIG. 10 illustrates an enlarged configuration of a single row in which the three delay circuits 5100 in FIG. 9 are connected to each other.

As illustrated in FIGS. 9 and 10, among the K first signal lines 3310, the i-th (where i is an integer of 1≤i≤K) signal line 33-$i$ is connected in common to the first switches 52-$i$ of the i-th capacitors 51-$i$ of a plurality of delay circuits 5100 arranged in the row direction. Therefore, the i-th first switches 52-$i$ of all of the delay circuits 5100 located in the same row in the sub-beam former 4000 can be simultaneously opened and closed by using a signal on the signal line 33-$i$. Consequently, the first switches 52-$i$ of the n delay circuits 5100 arranged in the same row can be opened and closed by using signals on a set of (K) first signal lines 3310 (signal lines 33-1 to 33-K).

As illustrated in FIG. 9, among the K second signal lines 3210, the j-th (where j is an integer of 1≤j≤K) signal line 32-$j$ is connected in common to the second switches 53-$j$ of the j-th capacitors 51-$j$ among the K capacitors 51 included in the respective m delay circuits 5100 arranged in the column direction. Therefore, the j-th second switches 53-$j$ of all of the delay circuits 5100 located in the same column in the sub-beam former 4000 can be simultaneously opened and closed by using a signal on the signal line 32-$j$. Consequently, the second switches 53-$j$ of the m delay circuits 5100 arranged in the same column can be opened and closed by using signals on a set of second signal lines 3210 (signal lines 32-1 to 32-K).

Herein, a description is made of a case where the first signal line 3310 is connected to the first switch 52, and the second signal line 3210 is connected to the second switch 53, but there may be a configuration in which the first signal line 3310 is connected to the second switch 53, and the second signal line is connected to the first switch 52.

The row direction sequencer 3300 sequentially outputs a signal (closing signal) for closing a switch for a predetermined time to the signal lines 33-1 to 33-K forming the K first signal lines 3310, at a predetermined time interval (clock signal) tc. In a case where the closing signal has been output to the K-th signal line 33-K, the row direction sequencer 3300 returns to the leading first signal line 33-1, and repeatedly performs an operation of outputting the closing signal. Consequently, the signal lines 33-1 to 33-K receiving the closing signal respectively close the first switches 52-1 to 52-K connected to the signal lines, and electric charge of signals which are input to the delay circuit 5100 from the input switching unit 54 and are to be delayed is "stored" (hereinafter, referred to as "written" in some cases) in the capacitors 51-1 to 51-K connected to the signal lines 33-1 to 33-K receiving the closing signal.

On the other hand, the column direction sequencer 3200 sequentially outputs a signal for closing a switch for a predetermined time to the signal lines 32-1 to 32-K forming the K second signal lines 3210, at a predetermined time interval tc. In a case where the closing signal has been output to the K-th signal line 32-K, the column direction sequencer 3200 returns to the leading first signal line 32-1, and repeatedly performs an operation of outputting the closing signal. Consequently, the signal lines 32-1 to 32-K receiving the closing signal respectively close the second switches 53-1 to 53-K connected to the signal lines, and electric charge stored in the capacitors 51-1 to 51-K connected to the closed second switches 53-1 to 53-K is "output" (hereinafter, referred to as "read" in some cases). The output signal is output to the vibrator 2111 or the summing unit 3400 from the output switching unit 55.

It is assumed that the column direction sequencer 3200 outputs a closing signal to the signal lines 32-1 to 32-K of the second signal lines 3210 in a state in which writing on all of the capacitors 51-1 to 51-K is completed.

Setting of Delay Amount

In such an operation of the delay circuit 5100, the row direction sequencer 3300 may relatively set the first delay amount by selecting a signal line to which a closing signal is initially output from among the signal lines 33-$i_F$, that is, a capacitor to which signal charge is initially written from among the capacitors 51-1 to 51-K. The column direction sequencer 3200 may set the second delay amount by selecting a signal line to which a closing signal is initially output from among the signal lines 32-$j_F$, that is, a capacitor from which signal charge is initially read from among the capacitors 51-1 to 51-K.

Such setting of a delay amount will be described with reference to FIG. 11. FIG. 11 is a block diagram illustrating the delay circuits 5100-11 to 5100-43 in which three delay circuits are arranged in the row direction, and four delay circuits are arranged in the column direction in FIG. 9.

The first delay amount is relatively defined according to a difference in a number $i_F$ of the capacitors 51-1 to 51-K to which signal charge is initially written between a certain delay circuit 5100 and another delay circuit 5100. In a case where a number ($i_F$=2) of the capacitor 51-1 to which signal charge is initially written in a certain delay circuit 5100-21 is one larger than a number ($i_F$=1) of the capacitor 51-1 to which signal charge is initially written in a delay circuit (for example, the delay circuit 5100-11) used as a reference, a first delay time is increased by a time obtained by applying the predetermined time interval tc to the difference therebetween. Therefore, by using any one of the delay circuits 5100 in a single sub-beam former 4000 as a reference, the row direction sequencer 3300 may set the first delay amount to be small by selecting a low number $i_F$ of the first signal lines 33-1 to 33-K to which a closing signal is initially output, and the first delay amount to be large by selecting a high number $i_F$ thereof.

The second delay amount is relatively defined according to a difference in a number $j_F$ of the capacitors 51-1 to 51-K from which signal charge is initially read between a certain delay circuit 5100 and another delay circuit 5100. In a case where a number ($j_F$=2) of the capacitor 51-2 from which signal charge is initially read in a certain delay circuit 5100-12 is one smaller than a number ($j_F$=3) of the capacitor 51-3 from which signal charge is initially read in a delay circuit (for example, the delay circuit 5100-11) used as a reference, a second delay time is increased by a time obtained by applying the predetermined time interval tc to the difference therebetween. Therefore, by using any one of the delay circuits 5100 in a single sub-beam former 4000 as a reference, the column direction sequencer 3200 may set the second delay amount to be large by selecting a low number $j_F$ of the capacitor 51 on which reading is initially performed (the second signal lines 32-1 to 32-K to which a closing signal is initially output), and the second delay amount to be small by selecting a high number $i_F$ thereof.

The entire delay amount for the delay circuits 5100 is defined by a sum of the first delay amount and the second delay amount. For example, as illustrated in FIG. 11, in a case where $i_F$=1, 2, 3, and 4 is set for the delay circuits 5100 of the first row to the fourth row in order, if the delay circuit 5100-11 of the first row is used as a reference delay circuit, with the first delay amount for the first row as a reference (=0), the first delay amount for the second row is +1×tc, the first delay amount for the third row is +2×tc, and the first delay amount for the fourth row is +3×tc. In a case where $j_F$=3, 2, and 1 is set for the delay circuits 5100 of the first to third columns in order, with the delay amount for the first delay circuit 5100 as a reference (=0), the second delay amount for the second column is +1×tc, and the second delay amount for the third column is +2×tc. Therefore, delay amounts for the delay circuits 5100-21, 5100-31, 5100-41, 5100-12 and 5100-13 are respectively (+1+0)×tc=tc, (+2+0)×tc=2tc, (+3+0)×tc=3tc, (+0+1)×tc=tc, and (+0+2)×tc=2tc, with a sum of the first delay amount and the second delay amount for the delay circuit 5100-11 as a reference. A delay amount for the delay circuit 5100-43 of the fourth row and the third column is (+3+2)×tc=5tc with respect to the delay amount for the reference delay circuit 5100-11.

FIG. 12(a) illustrates the arrangement of the respective delay circuits 5100 in FIGS. 9 and 11 and delay amounts. A delay amount corresponding to a sum of the first delay amount (row) and the second delay amount (column) is set for each delay circuit 5100 with respect to the delay circuit 5100 used as a reference (0). FIG. 12(b) illustrates that a change of the first delay amount due to selection of a number $i_F$ of the capacitor 51 on which initial writing is performed and a change of the second delay amount due to selection of a number $j_F$ of the capacitor 51 on which initial reading is performed are reserve to each other. FIG. 12 schematically illustrates that numbers $i_F$ and $j_F$ of the capacitors 51 on which initial writing and reading are performed are deviated (inclined) with respect to the rows and the columns due to increases in a row number and a column number, and thus a delay amount corresponding to a sum of the first delay amount (row) and the second delay amount (column) is set for each delay circuit as illustrated in FIG. 12(a).

In the above-described embodiment, the delay circuits 5100 which are divided into a plurality of sub-beam formers 4000 are arranged in the row direction and the column direction, the common first delay amount is set for a plurality of delay circuits arranged in the same row, and the common second delay amount is set for a plurality of delay circuit arranged in the same column. Therefore, desired delay of a transmission signal and sub-beam forming of a reception signal can be performed. Therefore, a delay amount can be set with a small number of signal lines compared with a case where control is performed by using a signal line independent for each delay circuit 5100. Therefore, it is possible to reduce a circuit scale of delay circuits in the ultrasonic probe 1000.

In the present embodiment, the capacitor 51 is used as a circuit delaying a signal in the delay circuit 5100, but, in the present embodiment, a circuit or an element having any configuration may be used as long as the circuit can set the first delay amount and the second delay amount, and can delay a signal by a delay amount obtained by adding both of the delay amounts together. Any configurations of the switches 52 and 53 may be used, and, for example, a MOSFET may be used.

The in-probe sub-beam former IC 2000 mounted with a plurality of sub-beam formers 4000 may employ any type of IC, and may employ a customized IC including an ASIC or an FPGA, and a combination of a plurality of ICs may be used.

There may be a configuration in which, as illustrated in FIG. 13, the first signal lines 3310 in the row direction and the second signal lines 3210 in the column direction are connected between the sub-beam formers. Consequently, it is possible to considerably reduce the number of signal lines required for control of a plurality of sub-beam formers 4000, and thus a circuit scale of delay circuits is further reduced.

Dynamic Focus

In the present embodiment, a dynamic focus process of changing a delay amount at each reception time point may be performed. In order to perform the dynamic focus process, a delay amount is required to be changed at a plurality of time points in transmission and reception events performed once, but it is desirable to reduce a transmission information amount between a circuit including the in-probe beam former 2000 and a system such as the delay amount calculation unit 200 or the main beam former 210 of the main body 1110. From this viewpoint, in a configuration of the present embodiment, control can be performed in the units of the sub-beam formers 4000 arranged vertically and horizontally, and thus a transmission information amount is small, and is excellent in terms of compressing of information. A writing/reading position selection operation on a plurality of delay circuits 5100 which are analog circuits can be controlled to be divided for partial set groups (groups of the sub-beam formers 4000) having symmetry regularly in a spatial cycle. Thus, it is possible to perform the dynamic focus process by reducing temporal/spatial grating lobes in a small information amount with high efficiency.

Setting of Maximum Delay Amount and Imaging Direction

In the present embodiment, the delay amount calculation unit 200 includes a maximum delay amount setting portion 220, and the maximum delay amount setting portion 220 sets the first delay amount and the second delay amount such that a sum of the first delay amount and the second delay amount set for each delay circuit 5100 is equal to or less than the maximum delay amount set in advance. For example, an upper limit of each of the first delay amount and the second delay amount is set on the basis of the maximum delay amount, and the first delay amount and the second delay amount are set to be equal to or less than the upper limits. Consequently, it is possible to minimize image quality deterioration due to a delay amount.

Specifically, a delay amount corresponding to the number (K) of the capacitors 51-1 to 51-K disposed in a single delay circuit 5100 is preferably set as the maximum delay amount. A time obtained by multiplying a time interval (clock signal) Tc at which the switches 52-1 to 52-K and 53-1 to 53-K of the K capacitors 51-1 to 51-K are sequentially closed by the number K of the capacitors 51 may be used as the maximum delay amount.

In this case, upper limits of the first delay amount and the second delay amount are preferably set according to an imaging direction. Specifically, the predefined maximum delay amount is allocated to the first delay amount and the second delay amount according to an imaging direction, and thus an upper limit thereof can be set. More specifically, the maximum delay amount is preferably allocated to an upper limit of the first delay amount and an upper limit of the second delay amount according to a ratio between an angle component (azimuth angle $\theta_A$) in a direction along a long axis direction of the ultrasonic probe and an angle component (elevation angle $\theta_E$) in a direction along a short axis direction of an angle formed between the imaging direction and a normal direction to the surface on which the vibrator array 2100 is arranged. Hereinafter, details thereof will be described.

FIG. 14 is a diagram for explaining imaging using the two-dimensional array probe 1000. A long axis direction of an arrangement surface of the vibrator array 2100 is set to an x axis, a direction orthogonal thereto is set to a y axis, and a normal direction of the arrangement surface (xy plane) of the vibrator array 2100 is set to a z axis. In FIG. 14, a fan-shaped range indicates an imaging range 6001. In a case of using a one-dimensional probe, the imaging range 6001 is restricted to a range (referred to as a long axis section) indicated by a fan shape in a plane including the x axis (long axis) and the z axis (normal line) as indicated by a thick solid line in FIG. 14(*a*), but, in the two-dimensional array probe 1000, a long axis tilt section obtained by rotating the long axis section about the x axis can be imaged. In the two-dimensional array probe 1000, as illustrated in FIG. 14(*b*), a range (referred to as a short axis section) indicated by a fan shape in a plane including the y axis (short axis) and the z axis (normal line) as indicated by a thick solid line in FIG. 14(*b*), and a short axis tilt section on the basis of by rotating the short axis section about the x axis, can be imaged. As illustrated in FIG. 14(*c*), a long axis rotation section obtained by rotating the long axis section about the z axis, or, as illustrated in FIG. 14(*d*), a section obtained by further rotating the long axis rotation section about the x axis can be imaged. In this case, in order to set a direction inclined in the x axis direction with respect to the normal direction (z axis) to the vibrator array 2100 of the probe 1000 as an imaging direction (a direction of a transmission focal point and a reception focal point), delay (second delay amount) in the column direction is necessary, and, in order to set a direction inclined in the y axis direction from the z axis as an imaging direction, delay (first delay amount) in the row direction is necessary. A delay amount obtained by adding the first delay amount to the second delay amount is a delay amount for a delay circuit. In order for a range deviated in an angle relative to the z axis direction to be able to be imaged, a large delay time is required to be secured, but, the maximum value of delay time is defined by the number of the capacitors 51-1 to 51-K included in the delay circuit 5100 connected to a single vibrator 2111. This will be hereinafter described with reference to FIGS. 15(*a*) to 15(*f*).

FIGS. 15(*a*) to 15(*f*) is a diagram for explaining a relationship between the arrangement of the capacitors 51-1 to 51-K and a delay amount, and illustrate a case where each of the delay circuits 5100 respectively corresponding to three vibrators (channels i, j and k) 2111 arranged in the column direction includes five (K=5) capacitors 51-1 to 51-5. For example, delay circuits respectively corresponding to the channels i, j and k are the delay circuits 5100-11, 5100-21 and 5100-31 illustrated in FIGS. 11 and 12(*a*). In FIGS. 15(*a*) to 15(*f*), write delay amounts for the delay circuits 5100-11, 5100-21 and 5100-31 corresponding to the channels i, j and k are respectively set to 0, 1, and 2 (×clock time Tc) by using the signal line 3310. As illustrated in FIG. 15(*a*), at a time point 0, nothing is written to the capacitors 51-1 to 51-5, and thus Null is written. In FIGS. 15(*b*) and 15(*c*), numbers written in rectangles indicating the capacitors 51-1 to 51-5 indicate data written to the capacitors, and, in a case where there is no delay during writing, 0 is written at a time point 1, 1 is written at a time point 2, and 2 is written at a time point 3. Hereinafter, similarly, if a time point is updated by 1, data is also updated by 1 and is written. After three clocks, a scene in which data is written to the first to third capacitors 51-1 to 51-3 in the delay circuit 5100-11 corresponding to the channel i with write delay of 0 is expressed by 0, 1, 2, Null, and Null, a scene in which data is written to the first and second capacitors 51-1 and 51-2 in the delay circuit 5100-21 corresponding to the channel j with write delay of 1 is expressed by 1, 2, Null, Null, and Null, and a scene in which data is written to the first capacitor 51-1 in the delay circuit 5100-31 corresponding to the channel k with write delay of 2 is expressed by 2, Null, Null, Null, and Null.

As illustrated in FIG. 15(*c*), data is written to all of the capacitors 51-1 to 51-5 after five clocks in the delay circuit 5100-11 corresponding to the channel i with write delay of 0. Therefore, after six or more clocks, as illustrated in FIGS. 15(*d*) to 15(*f*), data is overwritten to the first capacitor 51-1 and the subsequent capacitors again.

As mentioned above, pieces of data which are sequentially written to the capacitors 51-1 to 51-5 are read every clock in the same manner. The delay circuits 5100-11, 5100-21 and 5100-31 are arranged vertically, and thus data in the capacitors at the same position (the vertical column in FIG. 15) is read via the common signal line 3210. As illustrated in FIG. 15(*c*), for example, if, after five clocks, the data in the first capacitor 51-1 is read in each channel, after seven clocks, as illustrated in FIG. 15(*d*), the data in the third capacitor 51-3 is read, after ten clocks, as illustrated in FIG. 15(*e*), the data in the first capacitor 51-1 is read again, and, after fifteen clocks, as illustrated in FIG. 15(*f*), the data in the first capacitor 51-1 further again.

In this case, since delay can also be applied during reading, for example, after fifteen clocks, in FIG. 15(*f*), if read delay of 1 is applied, data in the second capacitor 51-2 is read. If read delay of 2 is applied, data in the third capacitor 51-3 is read, and, if read delay of 3 is applied, data in the fourth capacitor 51-4 is read. In this case, as is clear from numbers indicating delay amounts written in FIG. 15(*f*), it can be seen that delay amounts of data read from the capacitors 51-1 of the delay circuits 5100-11, 5100-21 and 5100-31 at a read delay amount of 0 are respectively 10, 11, and 12, and delay amounts of data read from the capacitors 51-2 at a read delay amount of 1 are respectively 11, 12, and 13 so as to be delayed by 1. Similarly, in a case where a read delay amount is 2, delay amounts of data read from the capacitors 51-3 at a read delay amount of 3 are respectively 12, 13, and 14 so as to be delayed by 1 compared with a case where a read delay amount is 1. However, in a case where a read delay amount is 3, delay amounts of data read from the capacitors 51-4 are respectively 13, 14, and 10, delay amounts for the delay circuits 5100-11 and 5100-12 are increased by 1, but, on the contrary, a delay amount for the delay circuit 5100-13 is reduced by 4. In other words, if a read delay amount is set to 3, in the delay circuit 5100-13, past data which is not consecutive temporally is read, and thus data which is not correctly delayed is read. Therefore, it can be seen that the maximum value of a read delay amount which can be set is 2. This indicates that, whereas the number K of the capacitors 51-1 to 51-K is 5, a delay amount of 3 is already used in write delay, and thus only delay of a maximum of 2 is applied to read delay. This phenomenon also occurs even if the number of capacitors 51 is changed or a delay amount during writing is changed. In other words, a sum of the maximum value of a delay amount during writing (first delay amount) and the maximum value of a delay amount during reading (second delay amount) is preferably set to be equal to or less than the number K (×clock time Tc) of capacitors. Through the setting, it is possible to prevent a phenomenon in which an actual delay amount of data is different from a desired delay amount, and thus to minimize image quality deterioration in an image in an imaging direction.

In the present embodiment, as illustrated in FIGS. 2 and 13, the delay amount calculation unit 200 includes the maximum delay amount setting portion 220. The maximum delay amount setting portion 220 sets upper limits of the first delay amount and the second delay amount according to an imaging direction. The delay amount calculation unit calculates the first delay amount and the second delay amount to be values of the upper limits or less. Consequently, a sum of the first delay amount and the second delay amount can be set to be equal to or less than a predefined maximum delay amount, that is, the number (×clock time Tc) of capacitors.

A description will be made of an operation of the maximum delay amount setting portion 220 by using a flow illustrated in FIG. 16. The main body 1110 includes a control unit 230, and the control unit 230 sets a plurality of scanning lines (imaging directions) on the basis of information regarding imaging conditions (the imaging range 6001, a transmission focal point, a reception focal point, and the like) received by an operation unit 240 from an operation. The maximum delay amount setting portion 220 includes a CPU and a memory storing a predetermined program in advance, and operates as in the flow of FIG. 16 by the CPU reading and executing the program in the memory. The maximum delay amount setting portion 220 may be formed of a programmable IC such as an FPGA, or an ASIC which is a customized IC.

First, the maximum delay amount setting portion 220 receives scanning line information (a direction from the imaging origin to a transmission focal point or a reception focal point) from the control unit 230 (step 161). For example, a value of a focal point coordinate (Fx,Fy,Fz) is received.

The maximum delay amount setting portion 220 calculates the azimuth angle $\theta_A$ and the elevation angle $\theta_E$ by solving simultaneous equations of Equation (1) (step 162).

$$Fx = D \sin \theta_A$$

$$Fy = D \cos \theta_A \sin \theta_E$$

$$Fz = D \cos \theta_A \cos \theta_E \qquad (1)$$

Here, D is a distance from the center (origin) of the surface of the two-dimensional vibrator array 2100 to a focal point, the azimuth angle $\theta_A$ is an angle component an in-surface direction including the x axis (long axis) and the z axis of an angle θ formed between the z axis (normal line) direction and an imaging direction, and the elevation angle $\theta_E$ is an angle component of the angle θ in an in-surface direction including the y axis (short axis) and the z axis.

Finally, the maximum delay amount obtained on the basis of the number K (×clock time Tc) of capacitors is allocated according to a ratio between absolute values of the azimuth angle $\theta_A$ and the elevation angle $\theta_E$ such that an upper limit of the first delay amount and an upper limit of the second delay amount are set (step 163). As described above, in order to set a direction (a direction of the azimuth angle $\theta_A$) inclined in the x axis direction with respect to the normal direction (z axis) to the vibrator array 2100 of the probe 1000 as an imaging direction, delay (second delay amount) in the column direction is necessary, and, in order to set a direction inclined in the y axis direction (a direction of the elevation angle $\theta_E$) from the z axis as an imaging direction, delay (first delay amount) in the row direction is necessary. Therefore, for example, in a case where an absolute value of the azimuth angle $\theta_A$ is $\theta_{A2}$, an absolute value of the elevation angle $\theta_E$ is $\theta_{E2}$, and a delay amount of zero is set for the center of the sub-beam former 4000, an upper limit of the second delay amount and an upper limit of the first delay amount are set according to the following Equations (2) and (3).

$$\text{Upper limit of second delay amount} = (K/2) \times (\theta_{A2}/(\theta_{A2} + \theta_{E2})) \qquad (2)$$

$$\text{Upper limit of first delay amount} = (K/2) - (\text{upper limit of second delay amount}) \qquad (3)$$

The delay amount calculation unit 200 generates an ideal delay amount for each vibrator 2111 corresponding to a distance from the focal point to each vibrator 2111 for each vibrator 2111 as illustrated in FIG. 17(a), generates an ideal delay amount for the sub-array 2110 corresponding to a distance between the focal point and the center of the sub-array 2110 as illustrated in FIG. 17(b), and obtains an ideal minute delay amount by obtaining a difference between both of delay amounts (FIG. 17(c); step 191 in FIG. 19). The delay amount calculation unit 200 cannot generate an ideal minute delay amount in a case where the first and second signal lines 3310 and 3210 among all of the sub-beam formers 4000 are connected as illustrated in FIG. 13, but determines initial delay values to be sent to the first and second signal lines such that a minute delay amount close thereto is obtained. An initial delay amount determined by the delay amount calculation unit 200 may be obtained through computation every time a focal point is changed, results computed for different focal points may be recorded on a recording medium in advance, and may be read, and an initial delay amount may be generated as a function of a variable, and may be recovered from the function. FIGS. 18(c) and 18(d) illustrate the second delay amount (column direction) and the first delay amount (row direction) for each number of the vibrator (channel) 2111 connected to the delay circuit 5100, and round marks connected to each other via a dotted line indicate initial delay amounts for the delay circuits 5100 arranged in a single column and a single row. The second delay amount (column direction) and the first delay amount (row direction) are indicated by the round marks in FIGS. 18(c) and 18(d) for each number of the vibrator (channel) 2111 connected to the delay circuit 5100. The round (O) marks connected to each other via the dotted line indicate initial delay amounts for the delay circuits 5100 arranged in a single column and a single row.

The delay amount calculation unit 200 adjusts the second delay amount and the first delay amount exceeding the upper limits thereof determined in step S163 to be equal to or less than the upper limits on the basis of the determined initial values of the second delay amount (column direction) and the first delay amount (row direction) (step 192). Triangular (Δ) marks connected to each other via a solid line in FIGS. 18(c) and 18(d) are adjusted delay values for the delay circuit 5100 arranged in a single column and a single row. In this case, only a delay amount exceeding the upper limit may be adjusted to a small value (a value close to zero), and all delay amounts for the same column or row including other delay amounts for the delay circuits arranged in the column or the row may be adjusted to be small values (values close to zero) at a predetermined proportion.

The delay amount calculation unit 200 sets the second delay amount (column direction) and the first delay amount (row direction) adjusted to be equal to or less than upper limit values for the column direction sequencer 3200 and the row direction sequencer 3300, respectively (step 193).

As mentioned above, the first and second delay amounts are adjusted to be equal to or less than the upper limit values which are set according to an azimuth angle and an elevation angle, and thus a sum of the first and second delay amounts can be made as close to an ideal delay amount as possible by taking into consideration an imaging direction. Hereinafter, this will be described by using actual simulation results.

For example, as an Example of simulation, it is considered that a single element has 0.3 mm square, and a virtual two-dimensional array probe 7000 is formed of 100×100 elements (in this case, any direction may be a long axis (×axis) direction). It is assumed that, in the two-dimensional vibrator array 2100, a single sub-array 2110 is formed of 4×5 elements. FIGS. 17(a) to 17(c) illustrate necessary delay amounts in a case where an ultrasonic wave is transmitted, as an imaging direction, in a direction in which a normal line of the vibrator array 2100 is inclined by 30 degrees in a long axis section, and is further rotated about the z axis by 35 degrees. A delay amount is standardized by the clock time Tc. Therefore, FIG. 17(a) illustrates an ideal delay amount for each of 100×100 vibrators 2111, FIG. 17(b) illustrates ideal delay amounts for 25×20 sub-arrays 2110, and FIG. 17(c) illustrates ideal minute delay amounts for the 100×100 vibrators.

FIGS. 18, 20 and 21 illustrate minute delay amounts in a case where the number K of capacitors 51 forming a single delay circuit 5100 is 26, and allocation to the first delay amount and the second delay amount is changed.

FIG. 18 illustrates an example in which the magnitude difference between the azimuth angle $\theta_A$ and the elevation angle $\theta_E$ is not great, and delay amounts are allocated to the first delay amount and the second delay amount in well balance. In a case where an absolute value of the azimuth angle $\theta_A$ is $\theta_{A2}$, and an absolute value of the elevation angle $\theta_E$ is $\theta_{E2}$, an integer value closest to a computation value of $(26/2)\times(\theta_{A2}/(\theta_{A2}+\theta_{E2}))$ is set as a second delay amount maximum value, and (26/2)−(second delay amount maximum value) is set as the first delay amount. FIG. 18(c) illustrates the second delay amounts given to the delay circuits 5100 in the column direction, in which the dashed line indicates a delay amount initial value in a case where there is no restriction in a delay amount, and the solid line indicates a delay amount adjusted in step S192 such that the delay amount is equal to or less than the upper limit value set in step S163. Similarly, FIG. 18(d) illustrates the first delay amounts given to the delay circuits 5100 in the row direction, in which the dashed line indicates a delay amount initial value, and the solid line indicates a delay amount adjusted to be equal to or less than the upper limit value.

FIG. 18(a) illustrates minute delay amounts adjusted in FIGS. 18(c) and 18(d) in the entire vibrator array 2100. FIG. 18(b) illustrates errors obtained by subtracting the adjusted minute delay amounts in FIG. 18(a) from the ideal minute delay amounts in FIG. 17(c). In the examples illustrated in FIG. 18, each of the first and second delay amounts has an upper limit, but the maximum delay amount is allocated to the first delay amount and the second delay amount in well balance, and thus the errors of the minute delay amounts in FIG. 18(b) are distributed to the column direction vibrator group and the row direction vibrator group, which are far away from the focal point.

On the other hand, FIG. 20 illustrates an example in which the absolute value $\theta_{A2}$ of the azimuth angle is considerably smaller than the absolute value $\theta_{E2}$ of the elevation angle, and a delay amount is preferentially allocated to the first delay amount. As is clear from FIGS. 20(c) and 20(d), an upper limit of the first delay amount is (26/2), and an ideal first delay amount is set without restriction. On the other hand, the second delay amount is set to have an upper limit of (26/2)−(first delay amount maximum value). In a case where an ideal delay amount of the first delay amount exceeds (26/2), the first delay amount is adjusted to the value (26/2), and thus the second delay amount becomes zero. In FIGS. 20(c) and 20(d), a dotted line indicates a delay amount initial value, and a solid line indicates a delay amount adjusted to be equal to or less than an upper limit value. It can be seen that the first delay amount in FIG. 20(d) is prioritized.

FIG. 20(a) illustrates minute delay amounts adjusted in FIGS. 20(c) and 20(d) in the entire vibrator array 2100. FIG. 20(b) illustrates errors obtained by subtracting the adjusted minute delay amounts in FIG. 20(a) from the ideal minute delay amounts in FIG. 17(c). In the examples illustrated in FIG. 20, a delay amount is preferentially allocated to the first delay amount, and thus errors in FIG. 20(b) concentrate on the row direction vibrator group far away from the focal point.

FIG. 21 illustrates an example in which the absolute value $\theta_{A2}$ of the azimuth angle is considerably greater than the absolute value $\theta_{E2}$ of the elevation angle, and a delay amount is preferentially allocated to the second delay amount. An upper limit of the second delay amount is (26/2), and ideal second delay amounts are set without being changed. An upper limit of the first delay amount is set to have an upper limit of (26/2)−(upper limit of second delay amount). In a case where an ideal value of the second delay amount exceeds (26/2), the maximum value of the second delay amount is adjusted to the value (26/2), and thus the first delay amount becomes zero. In FIGS. 21(c) and 21(d), a dotted line indicates a delay amount initial value, and a solid line indicates a delay amount adjusted to be equal to or less than an upper limit value. It can be seen that the second delay amount in FIG. 21(c) is prioritized.

FIG. 21(a) illustrates minute delay amounts adjusted in FIGS. 21(c) and 21(d) in the entire vibrator array 2100. FIG. 21(b) illustrates errors obtained by subtracting the adjusted minute delay amounts in FIG. 21(a) from the ideal minute delay amounts in FIG. 17(c). In the examples illustrated in FIG. 21, a delay amount is preferentially allocated to the second delay amount, and thus errors in FIG. 21(b) concentrate on the column direction vibrator group far away from the focal point.

With reference to FIGS. 22 to 24, a description will be made of an effect obtained in a case where a delay amount is allocated according to an imaging direction as described above.

FIG. 22 illustrates results of simulation of beam profiles when a sine wave is used of which a central frequency is 3 MHz, and a wave number is 1, in a case where a distance from the center of the vibrator array 2100 is 30 mm, and an imaging direction inclined by 40 degrees in a long axis section with respect to a normal direction of the vibrator array 2100, and there is a focal point in an imaging direction obtained by further rotating the imaging direction about the z axis by 35 degrees. In other words, this corresponds to a case where the azimuth angle $\theta_A$ is the same elevation angle $\theta_E$. FIG. 22(a) illustrates a simulation result of a beam profile with a solid line in a case of FIG. 18 in which a delay amount is allocated to the first delay amount and the second delay amount in well balance, FIG. 22(b) illustrates a simulation result of a beam profile with a solid line in a case of FIG. 21 in which a delay amount is preferentially allocated to the second delay amount, and FIG. 22(c) illustrates a simulation result of a beam profile with a solid line in a case of FIG. 20 in which a delay amount is preferentially allocated to the first delay amount. Dotted lines in FIGS. 22(a) to 22(c) indicate simulation results of beam profiles in a case where an ideal delay amount is used. From FIGS. 22(a) to 22(c), in a case where the azimuth angle $\theta_A$ is substantially the same as the elevation angle $\theta_E$, as illustrated in FIG. 21(a), a delay amount is preferably allocated to the first delay amount and the second delay amount in well balance.

FIG. 23 illustrates a case similar to the case illustrated in FIG. 22, but a case of an imaging direction inclined by 40 degrees in a long axis section with respect to the normal direction of the vibrator array 2100. That is, this corresponds to a case where the azimuth angle $\theta_A$ is considerably larger than the elevation angle $\theta_E$. As is clear from FIGS. 23(a) to 23(c), in a case where the azimuth angle $\theta_A$ is considerably larger than the elevation angle $\theta_E$, as illustrated in FIG. 23(b), a delay amount is preferably preferentially allocated to the second delay amount.

FIG. 24 illustrates a case similar to the case illustrated in FIG. 22, but a case where a position inclined by 40 degrees in a long axis section with respect to the normal direction of the vibrator array 2100 and then rotated about the z axis by 90 degrees is an imaging direction. That is, this corresponds to a case where the elevation angle $\theta_E$ is considerably larger than the azimuth angle $\theta_A$. As is clear from FIGS. 24(a) to 24(c), in a case where the elevation angle $\theta_E$ is considerably larger than the azimuth angle $\theta_A$, as illustrated in FIG. 24(c), a delay amount is preferably preferentially allocated to the first delay amount.

In the present embodiment, an allocation amount is determined on the basis of a radiation between the azimuth angle $\theta_A$ and the elevation angle $\theta_E$, but this is only an example, and any allocation amount may be used, for example, by changing a proportion of a weight, setting a sub-array size to an original size, or setting a proportion obtained in advance through a computation value or a test value. As illustrated in FIG. 20 or 21, in the example of preferentially allocating a delay amount to the first delay amount or the second delay amount, a description has been made of a method of giving a delay amount to the first delay amount or the second delay amount without restriction, but, this is only an example. For example, a priority method of adding a restriction condition such as a condition in which a delay amount on a non-prioritized side is not zero.

Sub-Array Mask

The delay amount calculation unit 200 may further include an error calculation portion 250 (refer to FIGS. 2 and 13) which calculates an error (for example, refer to FIGS. 18(b) and 25(a)) between a sum (for example, FIG. 18(a)) of the first delay amount and the second delay amount calculated in order to set a focal point in a desired imaging direction, and an ideal minute delay amount required to set a focal point in an imaging direction, and a sub-array mask 270.

The sub-array mask 270 of the delay amount calculation unit 200 may reset values which are different from the calculated first delay amount and second delay amount for the delay circuit 5100 in which an error calculated by the error calculation portion 250 is more than a predefined value. The sub-array mask 270 of the delay amount calculation unit 200 may replace an output from the delay circuit 5100 in which an error is more than a predefined value, with a differing value.

The image generation unit 260 of the main body 1110 generates an image of the imaging target 1300 by using a signal obtained by further delaying an output from the sub-beam former 4000 in the main beam former 210. There may be a configuration in which the image generation unit 260 calculates a sum of errors calculated by the error calculation portion 250 for each sub-beam former 4000, and does not use a delayed output from the delay circuit 5100 of the sub-beam former 4000 for generation of an image in a case where the sum of errors is more than a predefined value.

The sub-array mask 270 will be further described with reference to FIGS. 25 to 28.

FIG. 25 illustrates operations of the error calculation portion 250 and the sub-array mask 270. FIG. 25(a) illustrates an error (a minute delay error in the vibrator unit) relative to an ideal value of a minute delay amount in the same manner as FIGS. 18(b), 20(b) and 21(b). FIG. 25(b) is an enlarged view of a minute delay error of a single sub-array 2110 at the upper left end in FIG. 25(a). FIG. 25(c) illustrates an average of absolute values of minute delay errors of the vibrators 2111 forming the sub-array 2110 as an error of the sub-array 2110. FIG. 24(d) illustrates an example in which, in a case where the average of absolute values of minute delay errors in FIG. 24(c) is greater than a predefined threshold value, the sub-array is selected, and an output therefrom is not used. Herein, a value of $\frac{1}{13}$ of a wavelength is used as the threshold value. In other words, an output from the sub-array 2110 in which a minute delay amount error in the unit of the sub-array 2110 is more than an error amount corresponding to $\frac{1}{13}$ of a wavelength is cut.

In the same manner as in FIG. 22, FIGS. 26 to 28 illustrate results of simulation of beam profiles when a sine wave is used of which a central frequency is 3 MHz, and a wave number is 1, in a case where a distance from the center of the vibrator array 2100 is 30 mm, and an imaging direction inclined by 40 degrees in a long axis section with respect to a normal direction of the vibrator array 2100, and there is a focal point in an imaging direction obtained by further rotating the imaging direction about the z axis by 35 degrees. FIG. 26(a) illustrates a minute delay error set according to FIGS. 18(b) and 18(c) in which a delay amount is allocated to the first delay amount and the second delay amount in well balance. FIG. 26(b) illustrates an average of absolute values of minute delay errors of the vibrators 2111 forming the sub-array 2110 as an error of the sub-array 2110, and illustrates a state in which the sub-array mask 270 cuts the sub-array 2110 in which an error is equal to or more than a threshold value through threshold value processing. FIG. 26(c) illustrates a beam simulation result obtained by using only a sub-array which is not cut in the threshold value processing. It can be seen that side lobes are reduced in a solid line beam profile on which sub-array mask processing has been performed more than in a dotted line beam profile on which sub-array mask processing has not been performed as illustrated in FIG. 27(c).

FIGS. 27(a) to 27(c) and FIGS. 28(a) to 28(c) illustrate cases similar to the cases illustrated in FIGS. 26(a) to 26(c), but FIG. 27(a) illustrates an error in a case where a delay amount is preferentially allocated to the second delay amount in the same manner as in FIGS. 20(*c*) and 20(*d*), and FIG. 28(*a*) illustrates an error in a case where a delay amount is preferentially allocated to the first delay amount in the same manner as in FIGS. 21(*c*) and 21(*d*). FIGS. 27(*b*) and 28(*b*) illustrate a state in which the sub-array mask 270 cuts the sub-array 2110 in which an error is equal to or more than a threshold value through threshold value processing. FIGS. 27(*c*) and 28(*c*) illustrate beam simulation results obtained by using only a sub-array 2110 which is not cut in the threshold value processing. As is clear from FIGS. 27(*c*) and 28(*c*), it can be seen that side lobes are reduced in a solid line beam profile on which sub-array mask processing has been performed more than in a dotted line beam profile on which sub-array mask processing has not been performed. As mentioned above, it is possible to minimize image quality deterioration due to delay amount deficiency by applying a mask to a sub-array according to a delay error amount.

In FIG. 25(*c*), an average value of absolute values of minute delay errors of the vibrators of a single sub-array is used as an error in a sub-array, but is not limited thereto, and any value may be used as long as the value can express an error in the sub-array unit. In FIG. 25(*d*), a description has been made of an example of using an error amount corresponding to $1/13$ of a wavelength as a threshold value in threshold value processing, but this is only an example, and definition of threshold value processing may be changed depending on a direction or a depth. In FIGS. 26 to 28, a description has been made of a method of using only an output from a remaining sub-array on which threshold value processing has not been performed, but this is only an example. For example, during reception, all outputs from the sub-arrays may be used, but a weighting factor corresponding to an error amount may be applied to each sub-array. Values of the first delay amount and the second delay amount may be reset for the delay circuit 5100 of the sub-array 2110 in which an error is equal to or more than a predefined value. The sub-array mask 270 of the delay amount calculation unit 200 may replace an output from the delay circuit 5100 in which an error is more than a predefined value, with a differing value.

In FIG. 25(*b*), an error amount in a single sub-array is obtained, but is not limited thereto, and error processing may be performed with all sub-arrays arranged in a single column direction as a single unit, error processing may be performed with all sub-arrays arranged in a single row direction as a single unit, and threshold value processing corresponding to the column direction or the row direction may be performed.

In the above-described embodiment, the delay amount calculation unit 200 is disposed on the main body 1110, but may be mounted in the ultrasonic probe 1000.

REFERENCE SIGNS LIST

51 capacitor, 52 first switch, 53 second switch, 54 input switching unit, 55 output switching unit, 1000 probe, 1010 cable, 1100 ultrasonic imaging apparatus, 1020 connector box, 1110 main body, 1300 imaging target, 2000 substrate, 2100 vibrator array, 2110 sub-array, 2111 vibrator, 3100 transmission signal generation unit, 3200 column direction sequencer, 3210 (second) signal line, 3300 row direction sequencer, 3310 (first) signal line, 3400 summing unit, 4000 group (sub-beam former), 5100 delay circuit

The invention claimed is:
1. An ultrasonic imaging apparatus comprising:
   an ultrasonic probe having
   a plurality of vibrators arranged in a two-dimensional manner,
   delay circuits respectively connected to the plurality of vibrators, and
   a beam former integrated circuit (IC) provided with a plurality of signal lines for setting delay amounts for the delay circuits,
      wherein the delay circuits are built into the beam former IC; and
   a delay amount calculation unit that calculates the delay amounts for the delay circuits according to an imaging direction,
      wherein each of the delay circuits is configured to allow a first delay amount and a second delay amount to be set for each of the delay circuits, and to delay a signal by a signal delay amount obtained by adding the first delay amount and the second delay amount together,
      wherein the delay circuits are divided into a plurality of groups, and within each of the plurality of groups, the delay circuits are arranged in a row direction and a column direction,
      wherein, for each of the plurality of groups of the delay circuits, a common first delay amount is set for the delay circuits arranged in a same row using a first plurality of signal lines, and a common second delay amount is set for the delay circuits arranged in a same column using a second plurality of signal lines, and
      wherein the delay amount calculation unit calculates the first delay amount and the second delay amount such that a sum of the first delay amount and the second delay amount set for each of the delay circuits is equal to or less than a predefined maximum delay amount.

2. The ultrasonic imaging apparatus according to claim 1, further comprising:
   a maximum delay amount setting unit that sets an upper limit of each of the first delay amount and the second delay amount according to the imaging direction, and
   wherein the delay amount calculation unit calculates each of the first delay amount and the second delay amount to be equal to or less than the upper limit.

3. The ultrasonic imaging apparatus according to claim 2, wherein the maximum delay amount setting unit allocates the predefined maximum delay amount to the first delay amount and the second delay amount according to the imaging direction so as to set a value of the upper limit for each of the first delay amount and the second delay amount.

4. The ultrasonic imaging apparatus according to claim 3, wherein the maximum delay amount setting unit allocates the maximum delay amount to a first upper limit of the first delay amount and a second upper limit of the second delay amount according to a ratio between a first angle component in a first direction along a long axis direction of the ultrasonic probe and a second angle component in a second direction along a short axis direction of the ultrasonic probe,
   wherein the first angle component and the second angle component are o f an angle formed between the imaging direction and a normal direction to a surface on which the plurality of vibrators are arranged.

5. The ultrasonic imaging apparatus according to claim 1, wherein the delay amount calculation unit includes an error calculation portion that calculates an error between the sum of the first delay amount and the second delay amount calculated in order to set a focal point in the imaging direction and a delay amount required to set the focal point in the imaging direction.

6. The ultrasonic imaging apparatus according to claim 5, wherein the delay amount calculation unit sets delay amount value that is different from the first delay amount and the second delay amount for each of the delay circuits when the error is more than a predefined error value.

7. The ultrasonic imaging apparatus according to claim 5, wherein the delay amount calculation unit replaces an output from each of the delay circuits with a different value when the error is more than a predefined error value.

8. The ultrasonic imaging apparatus according to claim 5, further comprising:
an image generation unit that generates an image of an imaging target by using a delayed output obtained by delaying an output from one of the plurality if vibrators with its respective delay circuit, the one of the plurality of vibrators receiving an ultrasonic wave from the imaging direction of the imaging target,
wherein the image generation unit calculates a sum of errors,
wherein the errors are calculated by the error calculation portion for each of plurality of the group, and does not use the delayed output for the generation of the image in a case where the sum of errors is more than a predefined value for the sum of errors.

9. The ultrasonic imaging apparatus according to claim 1, wherein each of the delay circuits includes K capacitors connected in parallel to each other in order, and a first switch and a second switch respectively disposed on one side and the other side of each of the K capacitors.

10. The ultrasonic imaging apparatus according to claim 9, wherein the predefined maximum delay amount corresponds to a number of the K capacitors.

11. The ultrasonic imaging apparatus according to claim 1, wherein the signal lines for setting the common first delay amount for the delay circuits arranged in the same row in the pluarlity of groups are connected to each other between adjacent groups in the same row, and
wherein the signal lines for setting the common second delay amount for the delay circuits arranged in the same column in the plurality of groups are connected to each other between adjacent groups in the same column.

12. The ultrasonic imaging apparatus according to claim 1, wherein arrangement of the delay circuits in the row direction and the column direction in the group corresponds to the two-dimensional arrangement of the plurality of vibrators connected to the delay circuits.

13. An ultrasonic probe comprising:
a plurality of vibrators that are arranged in a two-dimensional manner;
delay circuits that are respectively connected to the plurality of vibrators;
a beam former integrated circuit (IC) that is provided with a plurality of signal lines for setting delay amounts for the delay circuits,
wherein the delay circuits are built into the beam former; and
a delay amount calculation unit that calculates the delay amounts for the delay circuits according to an imaging direction,
wherein each of the delay circuits is configured to allow a first delay amount and a second delay amount to be set for each of the delay circuits, and to delay a signal by a signal delay amount obtained by adding the first delay amount and the second delay amount together,
wherein the delay circuits are divided into a plurality of groups, and within each of the plurality of groups, the delay circuits are arranged in a row direction and a column direction,
wherein, for each of the plurality of groups of the delay circuits, a common first delay amount is set for the delay circuits in a same row using a first plurality of signal lines, and a common second delay amount is set for the delay circuits arranged in a same column using a second plurality of signal lines, and
wherein the delay amount calculation unit calculates the first delay amount and the second delay amount such that a sum of the first delay amount and the second delay amount set for each of the delay circuits is equal to or less than a predefined maximum delay amount.

* * * * *